US008808696B2

(12) United States Patent
Broly et al.

(10) Patent No.: US 8,808,696 B2
(45) Date of Patent: Aug. 19, 2014

(54) METHODS FOR THE TREATMENT AND PREVENTION OF ABNORMAL CELL PROLIFERATION USING TACI-FUSION MOLECULES

(75) Inventors: Herve Broly, Saint Selve (FR); Arnaud Ythier, Collex-Bossy (CH); Eric Sievers, Seattle, WA (US)

(73) Assignees: Ares Trading S.A., Aubonne (CH); Zymogenetics, Inc., Seattle, WA (US)

( * ) Notice: Subject to any disclaimer, the term of this patent is extended or adjusted under 35 U.S.C. 154(b) by 472 days.

(21) Appl. No.: 11/501,999

(22) Filed: Aug. 9, 2006

(65) Prior Publication Data

US 2007/0207156 A1    Sep. 6, 2007

Related U.S. Application Data

(60) Provisional application No. 60/706,888, filed on Aug. 9, 2005.

(51) Int. Cl.
*A61K 39/395* (2006.01)

(52) U.S. Cl.
USPC ........................................ 424/134.1; 514/7.9

(58) Field of Classification Search
None
See application file for complete search history.

(56) References Cited

U.S. PATENT DOCUMENTS

| 4,331,647 | A | 5/1982 | Goldenberg |
| 4,486,533 | A | 12/1984 | Lambowitz |
| 4,579,821 | A | 4/1986 | Palmiter et al. |
| 4,599,311 | A | 7/1986 | Kawasaki |
| 4,601,978 | A | 7/1986 | Karin |
| 4,615,974 | A | 10/1986 | Kingsman et al. |
| 4,656,134 | A | 4/1987 | Ringold |
| 4,661,454 | A | 4/1987 | Botstein et al. |
| 4,713,339 | A | 12/1987 | Levinson et al. |
| 4,784,950 | A | 11/1988 | Hagen et al. |
| 4,845,075 | A | 7/1989 | Murray et al. |
| 4,870,008 | A | 9/1989 | Brake |
| 4,882,279 | A | 11/1989 | Cregg |
| 4,931,373 | A | 6/1990 | Kawasaki et al. |
| 4,935,349 | A | 6/1990 | McKnight et al. |
| 4,946,778 | A | 8/1990 | Ladner et al. |
| 4,956,288 | A | 9/1990 | Barsoum |
| 4,977,092 | A | 12/1990 | Bitter |
| 4,990,446 | A | 2/1991 | Oberto et al. |
| 5,037,743 | A | 8/1991 | Welch et al. |
| 5,063,154 | A | 11/1991 | Fink et al. |
| 5,139,936 | A | 8/1992 | Botstein et al. |
| 5,143,830 | A | 9/1992 | Holland et al. |
| 5,155,027 | A | 10/1992 | Sledziewski et al. |
| 5,162,222 | A | 11/1992 | Guarino et al. |
| 5,162,228 | A | 11/1992 | Sumino et al. |
| 5,208,146 | A | 5/1993 | Irie |
| 5,223,409 | A | 6/1993 | Ladner et al. |
| 5,403,484 | A | 4/1995 | Ladner et al. |
| 5,523,227 | A | 6/1996 | Bram et al. |
| 5,541,291 | A | 7/1996 | Keene |
| 5,567,584 | A | 10/1996 | Sledziewski et al. |
| 5,571,698 | A | 11/1996 | Ladner et al. |
| 5,595,721 | A | 1/1997 | Kaminski et al. |
| 5,637,677 | A | 6/1997 | Greene et al. |
| 5,650,550 | A | 7/1997 | Korach et al. |
| 5,693,762 | A | 12/1997 | Queen et al. |
| 5,716,808 | A | 2/1998 | Raymond |
| 5,736,383 | A | 4/1998 | Raymond |
| 5,739,277 | A | 4/1998 | Presta et al. |
| 5,969,102 | A | 10/1999 | Bram et al. |
| 6,015,801 | A * | 1/2000 | Daifotis et al. ............... 514/108 |
| 6,316,222 | B1 | 11/2001 | Bram et al. |
| 6,500,428 | B1 | 12/2002 | Bram et al. |
| 6,537,540 | B1 | 3/2003 | Burstein et al. |
| 6,716,576 | B1 | 4/2004 | Yu et al. |
| 6,774,106 | B2 | 8/2004 | Theill et al. |
| 7,501,487 | B1 | 3/2009 | Mangelsdorf et al. |
| 2003/0022233 | A1 | 1/2003 | Goodwin |
| 2003/0103986 | A1 | 6/2003 | Rixon et al. |
| 2004/0013674 | A1 | 1/2004 | Ambrose et al. |
| 2005/0042009 | A1 | 2/2005 | Roztocil et al. |
| 2005/0070689 | A1 | 3/2005 | Dixit et al. |
| 2005/0163775 | A1 | 7/2005 | Chan et al. |
| 2005/0183148 | A1 | 8/2005 | Bram et al. |
| 2006/0034852 | A1 | 2/2006 | Rixon et al. |
| 2006/0067933 | A1 | 3/2006 | Gross et al. |
| 2006/0073146 | A1 | 4/2006 | Ashkenazi |
| 2006/0286093 | A1 | 12/2006 | Gross et al. |
| 2007/0071760 | A1 | 3/2007 | Broly et al. |

(Continued)

FOREIGN PATENT DOCUMENTS

| AU | 2006201472 A1 | 5/2006 |
| EP | 0869180 A1 | 10/1998 |

(Continued)

OTHER PUBLICATIONS

Stein et al, (Journal of Cancer Research and Clinical Oncology 101(1):p. 29 abstract, 1981).*
Martino, FierceBiotech, pp. 1-4. Nov. 9, 2006 Zymogenics and Serono to Begin TACI-IG Cinical Studies in B-Cell Malignancies, first reported Business Wire—Oct. 4, 2004.*
Wang et al, Nature Immunology, 2(7):632-636, 2001).*
Jelinek, D. (Myeloma Today, 6(6):1-34, 2005).*
Moreaux et al, Blood 103(8):3148-3157, 2004.*
Gross et al (Immunity, 15:289-302, 2001).*

(Continued)

*Primary Examiner* — Patricia A Duffy
(74) *Attorney, Agent, or Firm* — Morgan, Lewis & Bockius LLP

(57) ABSTRACT

The present invention provides methods and compositions for treatment of hyperproliferative disorders and cancers, including multiple myeloma and Waldenström's macroglobulinemia, comprising administering to a patient in need of the treatment a TACI-Ig fusion molecule in amount sufficient to suppress proliferation-inducing functions of BlyS and APRIL.

16 Claims, 8 Drawing Sheets

(56) References Cited

U.S. PATENT DOCUMENTS

| | | | |
|---|---|---|---|
| 2007/0264689 A1 | 11/2007 | Gross et al. | |
| 2007/0269443 A1* | 11/2007 | Kalled et al. | 424/153.1 |
| 2009/0209006 A1 | 8/2009 | Rixon et al. | |

FOREIGN PATENT DOCUMENTS

| | | |
|---|---|---|
| EP | 1666052 A | 6/2006 |
| GB | 9828628.9 | 12/1998 |
| WO | WO 91/11465 | 8/1991 |
| WO | WO 94/06463 | 3/1994 |
| WO | WO 94/09137 | 4/1994 |
| WO | WO 95/35501 | 12/1995 |
| WO | WO 96/18641 | 6/1996 |
| WO | WO 96/27011 | 9/1996 |
| WO | WO 97/09137 | 3/1997 |
| WO | WO 97/17450 | 5/1997 |
| WO | WO 97/17451 | 5/1997 |
| WO | WO 97/33902 | 9/1997 |
| WO | WO 98/02536 | 1/1998 |
| WO | WO 98/02565 | 1/1998 |
| WO | 98/27114 | 6/1998 |
| WO | 98/18921 | 7/1998 |
| WO | 98/39361 | 9/1998 |
| WO | WO 98/39361 | 9/1998 |
| WO | 98/55620 | 12/1998 |
| WO | WO 98/55621 | 12/1998 |
| WO | WO 99/04001 | 1/1999 |
| WO | 99/12964 | 3/1999 |
| WO | WO 99/11791 | 3/1999 |
| WO | WO 99/12965 | 3/1999 |
| WO | WO 00/03995 | 1/2000 |
| WO | 00/39295 | 7/2000 |
| WO | 00/40716 | 7/2000 |
| WO | 00/43032 | 7/2000 |
| WO | 00/50597 | 8/2000 |
| WO | WO 00/62790 | 10/2000 |
| WO | 00/67034 | 11/2000 |
| WO | 01/12812 A2 | 2/2001 |
| WO | 01/24811 A1 | 4/2001 |
| WO | WO 01/60397 | 8/2001 |
| WO | WO 01/77342 | 10/2001 |
| WO | WO 01/81417 A2 | 11/2001 |
| WO | WO 01/87977 | 11/2001 |
| WO | PCT/JP01/06944 | 2/2002 |
| WO | WO 02/14504 | 2/2002 |
| WO | WO 02/38766 | 5/2002 |
| WO | 02/066516 A2 | 8/2002 |
| WO | WO 02/094852 A2 | 11/2002 |
| WO | WO 03/01877 | 1/2003 |
| WO | 03/014294 A2 | 2/2003 |
| WO | WO 03/055979 | 7/2003 |
| WO | 03/097040 A1 | 11/2003 |
| WO | 2005/005462 A2 | 1/2005 |
| WO | 2005/042009 A1 | 5/2005 |
| WO | WO 2006/052493 | 5/2006 |
| WO | WO 2006/068867 | 6/2006 |
| WO | 2007/019573 A2 | 2/2007 |
| WO | 2007/019575 A2 | 2/2007 |
| WO | WO 2007/019618 | 2/2007 |
| WO | WO 00/40714 A2 | 7/2007 |
| WO | WO 2007/134326 | 11/2007 |
| WO | 2009/062960 A1 | 5/2009 |

OTHER PUBLICATIONS

Barlogie, B., et al. Extended Survival in Advanced and Refractory Multiple Myeloma After Single-Agent Thalidomide: Identification of Prognostic Factors in a Phase 2 Study of 169 Patients, Blood, vol. 98, No. 2, pp. 492-494 (2001).

Cheema, G., et al., "Elevated Serum B Lmphocyte Stimulator Levels in Patients With Systemic Immune-Based Rheumatic Diseases," Arthritis & Rheumatism, vol. 44., No. 6, pp. 1313-1319 (2001).

Cheson, B., et al., "National Cancer Institute-Sponsored Working Group Guidelines for Chronic Lymphocytic Leukemia: Revised Guidelines for Diagnosis and Treatment," Blood, vol. 87, No. 12, pp. 4990-4997 (1996).

Do, R., "Attenuation of Apoptosis Underlies B Lymphocyte Stimulator Enhancement of Humoral Immune Response." J. Exp. Med., vol. 192, No. 7, pp. 953-964 (2000).

Groom, J., et al., "Association of BAFF/BLyS Overexpression and Altered B Cell Differentiation With Sjogren's Syndrome," The Journal of Clinical Investigation, vol. 109, No. 1, pp. 59-68 (2002).

Gross, J., et al., "TACI and BCMA are Receptors for a TNF Homologue Implicated in B-Cell Autoimmune Disease," Nature, vol. 404, pp. 995-999 (2000).

Gross, J., et al., "TACI-Ig Neutralizes Molecules Critical for B Cell Development and Autoimmune Disease: Impaired B Cell Maturation in Mice Lacking BLyS," vol. 15, pp. 289-302 (2001).

Hahne, M., et al., "APRIL, a New Ligand of the Tumor Necrosis Factor Family, Stimulates Tumor Cell Growth," Journal of Experimental Medicine, vol. 188, No. 6, pp. 1185-1190 (1998).

Kelly, K., "APRIL/TRDL-1, a Tumor Necrosis Factor-Like Ligand, Stimulates Cell Death," Cancer Research, vol. 60, pp. 1021-1027 (2000).

Mackay, F., et al., "Mice Transgenic for BAFF Develop Lymphocytic Disorders Along with Autoimmune Manifestations," J. Exp. Med., vol. 190, No. 11, pp. 1697-1710 (1999).

Mariette, X., et al., "The Level of BLyS (BAFF) Correlates with the Titre of Autoantibodies in Human Sjogren's Syndrome," Annals of the Rheumatic Diseases, vol. 62, pp. 168-171 (2003).

Marsters, S., et al., "Interaction of the TNF Homologues BLyS and APRIL with the TNF Receptor Homologues BCMA and TACI," Current Biology, vol. 10, pp. 785-788 (2000).

Moore, P., et al., "BLyS: Member of the Tumor Necrosis Factor Family and B Lymphocyte Stimulator," Science, vol. 285, pp. 260-263 (1999).

Richardson, P., et al., "A Phase 2 Study of Bortezomib in Relapsed, Refractoroy Myeloma," N Engl J Med, vol. 348, No. 26, pp. 2609-2617 (2003).

Roschke, V., et al., "BLyS and APRIL Form Biologically Active Heterotrimers That Are Expressed in Patients with Systemic Immune-Based Rheumatic Diseases," Journal of Immunology, vol. 169, pp. 4314-4321 (2002).

Schneider, P., et al., "BAFF, A Novel Ligand of the Tumor Necrosis Factor Family, Stimulates B Cell Growth," J. Exp. Med., vol. 189, No. 11, pp. 1747-1756 (1999).

Thompson, J., et al., "BAFF-R, a Newly Identified TNF Receptor That Specifically Interacts with BAFF," Science, vol. 293, pp. 2108-2111 (2001).

International Search Report, PCT/US2006/031277, Sep. 5, 2007.

International Search Report of PCT/US2006/031274, dated Apr. 30, 2007.

Anonymous, "Waldenstrom Macroglobulnemia." Wikipedia, The Free Encyclopedia, http://en.wikipedia.org/wiki/Waldenstrom's_macroglobulinemai.

Martino, FierceBiotech, Press Release: ZymoGenetics and Serono to Begin TACI-Ig Clinical Studies in B-cell Malignancies, pp. 1-4, Nov. 9, 2006.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology 111:2129-2138 (Nov. 1990).

Lazar et al., "Transforming Growth Factor alpha: Mutation of Aspartic Acid 47 and Leucine 48 Results in Different Biological Activities" Molecular and Cellular Biology 8(3) 1247-1252 (1988).

Schwartz et al., "A Superactive Insulin: [B10-Aspartic acid] insulin (human)" Proc Natl Acad Sci USA 84:6408-6411 (1987).

Lin et al., "Structure-Function Relationships in Glucagon: Properties of Highly Purified Des-His1, Monoiodo-, and [Des-Asn 28,Thr29](homoserine lactone27)-glucagon" Biochemistry USA 14:1559-1563 (1975).

Brenner, S., et al., "Errors in Genome Annotation," Trends in Genetics, vol. 15, pp. 132-133 (1999).

Davidson and Diamond, "Autoimmune Diseases," N Engl J Med, vol. 345, No. 5, pp. 340-350 (Aug. 2, 2001).

Ding and Jones, "Belimumab Human Genome Sciences/Cambridge Antibody Technology," Current Opinion in Investigational Drugs, vol. 7, No. 5, pp. 464-472 (2006).

(56) References Cited

OTHER PUBLICATIONS

Eisen, "Aberrant Immune Responses," General Immunology, J.B. Lippincott Company, pp. 215-225 (1990).
Falk, et al., "The Systemic Amyloidoses," N Engl J Med, vol. 337, No. 13, pp. 898-909 (Sep. 25, 1997).
Feldmann, et al., "Evaluation of the Role of Cytokines in Autoimmune Disease: The Importance of TNFa in Rheumatoid Arthritis," Progress in Growth Factor Research, vol. 4, pp. 247-255 (1992).
Feldmann and Maini, "The Role of Cytokines in the Pathogenesis of Rheumatoid Arthritis," Rheumatology, vol. 38, Suppl. 2, pp. 3-7 (1999).
Ginzler, et al., "Safety Pharmacokinetic and Pharmacodynamic Results of a Phase 1 Single and Double Dose-Escalation Study of LymphoStat-B (Human Monoclonal Antibody to BLyS) in SLE Patients," American College of Rheumatology Abstract Supplement, pp. S377 (Oct. 26, 2003).
Gras, et al., "BCMAp: An Integral Membrane Protein in the Golgi Apparatus of Human Mature B Lymphocytes," International Immunology, vol. 7, No. 7, pp. 1093-1106 (Mar. 28, 1995).
Halpern et al., "Chronic Administration of Belimumab, a BLyS Antagonist, Decreases Tissue and Peripheral Blood B-Lymphocyte Populations in Cynomolgus Monkeys: Pharmacokinetic, Pharmacodynamic, and Toxicologic Effects," Toxicological Sciences, vol. 91, No, 2, pp. 586-599 (2006).
Huard, et al., "BAFF Production by Antigen-Presenting Cells Provides T Cell Co-Stimulation," International Immunology, vol. 16, No. 3, pp. 467-475 (2004).
Huard, et al "T Cell Costimulation by the TNF Ligand BAFF," Journal of Immunology, vol. 167, pp. 6225-6231 (2001).
Hymowitz, et al., "Structures of APRIL-Receptor Complexes," Journal of Biological Chemistry, vol. 280, No. 8, pp. 7218-7227 (2005).
Ibragimova, G., et al., "Stability of the B-Sheet of the WW Domain: A Molecular Dynamics Simulation Study," Biophysical Journal, vol. 77, pp. 2192-2198 (1999).
International Search Report for WO 99/12964 dated Apr. 13, 1999.
International Search Report of PCT/US2007/068982 dated Mar. 3, 2008.
Laabi, et al., "A New Gene, BCM, on Chromosome 16 is Fused to the Interleukin 2 Gene by a t(4;16) (q26;p13) Translocation in a Malignant T Cell Lymphoma," EMBO Journal, vol. 11, No. 11, pp. 3897-3904 (1992).
Laabi, et al., "The BCMA Gene, Preferentially Expressed During B Lymphoid Maturation, is Bidirectionally Transcribed," Nucleic Acids Research, vol. 22, No. 7, pp. 1147-1154 (1994).
Madry, "The Characterization of Murine BCMA Gene Defines it as a New Member of the Tumor Necrosis Factor Receptor Superfamily," International Immunology, vol. 10, No. 11, pp. 1693-1702 (Aug. 3, 1998).
Moon and Ryu, "TACI: Fc Scavenging B Cell Activating Factor (BAFF) Alleviates Ovalbumin-Induced Bronchial Asthma in Mice," Exp. Mol. Med., vol. 39, No. 3, pp. 343-352 (Jun. 2007).
Mukhopadhyay, et al., "Identification and Characterization of a Novel Cytokine, THANK, a TNF Homologue That Activates Apoptosis, Nuclear Factor-kB, and c-Jun NH2-Terminal Kinase," Journal of Biological Chemistry, vol. 274, No. 23, pp. 15978-15981 (1999).
Munafo, et al., "Safety, Pharmacokinetics and Pharmacodynamics of Atacicept in Healthy Volunteers," Eur J Clin Pharmacol, vol. 63, pp. 647-656 (Apr. 2, 2007).
Ng, et al., "B Cell-Activating Factor Belonging to the TNF Family (BAFF)-R Is the Principal BAFF Receptor Facilitating BAFF Costimulation of Circulating T and B Cells," Journal of Immunology, vol. 173, pp. 807-817 (2004).
Panayi, "The Pathogenesis of Rheumatoid Arthritis: From Molecules to the Whole Patient," British Journal of Rheumatology, vol. 32, pp. 533-536 (1993).
Patel, et al., "Engineering an APRIL-specific B Cell Maturation Antigen," Journal of Biological Chemistry, vol. 279, No. 16, pp. 16727-16735 (Apr. 16, 2004).
Ramakrishnan and Scheid, "Diagnosis and Management of Acute Pyelonephritis in Adults," American Family Physician, vol. 71, No. 5, pp. 933-942 (Mar. 1, 2005).
Ramanujam M. et al., "Mechanism of Action of Transmembrane Activator and Calcium Modulator Ligand Interactor-Ig in Murine Systemic Lupus Erythematosus," J. Immunol., vol. 173, 3524-3534 (2004).
Smith, T., et al., "The Challenges of Genome Sequene annotation or The devil is in the details," Nature Biotechnology, vol. 15, 1222-1223 (1997).
Strand V. et al., "Biologic Therapies in Rheumatology: Lessons Learned, Future Directions," Nat. Rev. Drug. Discov., vol. 6, No. 1, 75-92 (2007).
Suntharalingam G., et al., "Cytokine Storm in a Phase 1 Trial of the Anti-CD28 Monoclonal Antibody TGN1412," N. Engl. J. Med., vol. 355, 1018-1028 (2006).
Thompson, et al., "BAFF Binds to the Tumor Necrosis Factor Receptor-like Molecule B Cell Maturation Antigen and is Important for Maintaining the Peripheral B Cell Population," J. Exp. Med., vol. 192, No. 1, pp. 129-135 (Jul. 3, 2000).
Tsokos, "Lymphocytes, Cytokines, Inflammation, and Immune Trafficking," Current Opinion in Rheumatology, vol. 7, pp. 376-383 (1995).
Von Bulow and Bram, "NF-AT Activation Induced by a CAML-Interacting Member of the Tumor Necrosis Factor Receptor Superfamily," Science, vol. 278, pp. 138-141 (Oct. 3, 1997).
Wallach, "TNF Ligand and TNF/NGF Receptor Families," Dept of Biological Chemistry, Weizmann Institute of Science, pp. 377-411 (2000).
Wang, et al., "TACI-Ligand Interactions are required for T Cell Activation and Collagen-Induced Arthritis in Mice," Nature Immunology, vol. 2, No. 7, pp. 632-637 (2001).
Xia et al., "TACI is a TRAF-Interacting Receptor for TALL-1, a Tumor Necrosis Factor Family Member Involved in B Cell Regulation," J. Exp. Med., vol. 192, No. 1, pp. 137-143 (Jul. 3, 2000).
Yan M., et al., "Activation and Accumulation of B Cells in TACI-Deficient Mice," Nat. Immunol., vol. 2, 638-643 (2001).
U.S. Appl. No. 11/502,134—Non-final office action dated Sep. 27, 2007.
U.S. Appl. No. 11/502,134—Final office action dated Jul. 2, 2008.
U.S. Appl. No. 11/502,134—Advisory Action Communication dated Dec. 16, 2008.
U.S. Appl. No. 11/502,134—Non-final office action dated Mar. 12, 2009.
U.S. Appl. No. 11/748,978—Restriction requirement dated Feb. 13, 2008.
U.S. Appl. No. 11/748,978—Non-final office action dated May 30, 2008.
U.S. Appl. No. 11/748,978—Final office action dated Jan. 8, 2009.
Altschul, et al., Bull Math. Bio., vol. 48, pp. 603-666 (1986).
Anolik, J.H., et al., "New Treatments for SLE: Cell-Depleting and Anti-Cytokine Therapies," Best Practice & Research Clinical Rheumatology, vol. 19, No. 5, pp. 859-878 (2005).
Aviv, H., et al., "Purificaton of Biologically Active Globin Messenger RNA by Chromatography on Oligothymidylic acid Cellulose," Proc. Natl. Acad. Sci., vol. 69, pp. 1408-1412 (1972).
Bairoch, A., "The PROSITE Dictionary of Sites and Patterns in Proteins, Its Current Status," Nucleic Acids Research, vol. 21, No. 13, pp. 3097-3103 (1993).
Bell, E., "TNF-R Homologues in Autoimmune Disease," Immunology Today, vol. 21, No. 6, p. 253 (Jun. 1, 2000).
Bilsborough, J., et al., "TACI-Ig Prevents the Development of Airway Hyper-Responsiveness in a Murine Model of Asthma," pp. 1-34.
Biosis Database, [online], Biosciences Information Service, Philadelphia, PA (Sep. 2008). Carbonatto, Michela, et al., Nonclinical Safety, Pharmacokinetics, and Pharmacodynamics of Atacicept, Database Accession No. PRV200800586339, Toxicological Sciences, vol. 105, No. 1, pp. 200-210 (Sep. 2008).
Bird, et al., Science, vol. 242, p. 423 (1988).
Birren, et al., EMBL Database Report for Accession No. AC003958, Jan. 6, 1998 (XP-002072294).

(56) References Cited

OTHER PUBLICATIONS

Bodmer, et al., "The Molecular Architecture of the TNF Superfamily," Trends in Biochemical Sciences, vol. 27, No. 1, pp. 19-24 (Jan. 2002).
Bonning, et al., J. Gen. Virol., vol. 75, pp. 1551-1556 (1994).
Bram, R.J. and G.R. Crabtree, "Calcium Signalling in T Cells Stimulated by a Cyclophilin B-Binding Protein," Nature, vol. 371, pp. 355-358 (Sep. 22, 1994).
Bram, R.J., et al., "Identification of the Immunophilins Capable of Mediating Inhibition of Signal Transduction by Cyclosporin A and FK506: Roles of Calcineurin Binding and Cellular Location," Molecular and Cellular Biology, vol. 13, No. 8, pp. 4760-4769 (Aug. 1993).
Carter, et al., Proc. Nat. Acad. Sci., vol. 89, p. 42875 (1992).
Chan, A., et al., "Rescue Therapy Anti-CD20 Treatment in Neuroimmunologic Breakthrough Disease," J. Neurol. vol. 254, pp. 1604-1606 (2007).
Chazenbalk, Rapport, J. Biol. Chem., vol. 270, pp. 1543-1549 (1995).
Chirgwin, et al., Biochemistry, vol. 18, pp. 52-94 (1979).
Ciccarone, et al., Focus, vol. 15, p. 80 (1993).
Claros, M.G., et al., Comput. Appl. Biosci., vol. 10, pp. 685-686 (1994).
Clipstone, N.A. and G.R. Crabtee, "Identification of Calcineurin as a Key Signalling Enzyme in T-lymphocyte Activation," Nature, vol. 357, pp. 695-697 (Jun. 25, 1992).
Corsaro, Pearson Somatic Cell Genetics, vol. 7, p. 603 (1981).
Cosman, Stem Cells, vol. 12, pp. 440-455 (1994).
Courtenay-Luck, et al., "Genetic Manipulation of Monoclonal Antibodies, Cambridge University Press article, Monoclonal Antibodies, Production, Engineering and Clinical Application," p. 166 (1995).
Crabtee and Clipstone, Annu. Rev. Biochem., vol. 63, pp. 1045-1083 (1994).
Cyster, Nature Immunol., vol. 1, pp. 9-10 (2000).
Dall'Era, M., et al., Atacicept Reduces B Lymphocytes and Immunoglobulin Levels in Patients with Sytsemic Lupus Erythematosus (SLE), pp. 1-35.
Database Accession No. 014836, "Tumor Necrosis Factor Receptor Superfamily Member 13B" (2007).
Database Accession No. P20333, "Tumor Necrosis Factor Receptor 2 Precursor," (1995).
DiLillo, D.J., et al., "Maintenance of Long-Lived Plasma Cells and Serological Memory Despite Mature and Memory B Cell Depletion during CD20 Immunotherapy in Mice," The Journal of Immunology, vol. 180, pp. 361-371 (2008).
Durfee, T., et al., Genes Dev., vol. 7, pp. 555-569 (1993).
Dynan, T., Nature, vol. 316, pp. 774-778 (1985).
Emmel, E.A., et al., "Cyclosporin A Specifically Inhibits Function of Nuclear Proteins Involved in T Cell Activation," Science, vol. 246, pp. 1617-1620 (Dec. 22, 1989).
European Search Report of EP 05020384.3 dated Apr. 27, 2007.
European Search Report of EP 03016020 dated Jul. 10, 2003.
European Search Report of EP 05018984 dated Jan. 25, 2006.
European Search Report of EP 05018985 dated Jan. 16, 2006.
European Supplementary & Partial Search Report of EP 02734478 dated Dec. 7, 2007.
Excoffon, K., et al., "The Role of the Extracellular Domain in the Biology of the Coxsackievirus and Adenovirus Receptor," Am. J. Respir. Cell. Mol. Biol., vol. 32, pp. 498-503 (2005).
Fiering, S., et al., "Single Cell Assay of a Transcription Factor Reveals a Threshold in Transcription Activated by Signals Emanating from the T-cell Antigen Receptor," Genes & Development, vol. 4, pp. 1823-1834 (1990).
Friedman, J. and I. Weissman, "Two Cytoplasmic Candidates for Immunophilin Action Are Revealed by Affinity for a New Cyclophilin: One in the Presence and One in the Absence of CsA," Cell, vol. 66, pp. 799-806 (Aug. 23, 1991).
Gao, X., et al., "Advanced Transgenic and Gene-Targeting Approaches," Neurochemical Research, vol. 24, No. 9, pp. 1181-1188 (1999).

Garnier, et al., Cytotechnol., vol. 15, pp. 145-155 (1994).
Gleeson, et al., J. Gen. Microbiol., vol. 132, pp. 3459-3465 (1986).
Graham, et al., J. Gen. Viol., vol. 36, pp. 59-72 (1977).
Graham, Van der EB, Virology, vol. 52, p. 456 (1973).
Grantham, et al., Nuc.Acids Res., vol. 8, pp. 1893-1912 (1980).
Green, et al., Nat. Genet, vol. 7, p. 13 (1994).
Grosjean, Fiers, Gene, vol. 18, pp. 199-209 (1982).
Grussenmeyer, et al., Proc. Natl. Acad. Sci., vol. 82, pp. 7952-7954 (1985).
Haas, et al., Cur. Biol., vol. 6, pp. 315-324 (1996).
Hatzoglou, et al., J. Immunol., vol. 165, pp. 1322-1330 (2000) (XP002324045).
Hawley-Nelson, et al., Focus, vol. 15, p. 73 (1993).
Herrscher, R.F., et al., "The Immunoglobulin Heavy-chain Matrix-Associating Regions are Bound by Bright α B Cell-Specific Trans-Activator That Describes a New DNA-Binding Protein Family," Genes & Development, vol. 9, pp. 30607-3082 (1995).
Hillier, et al., GenBank Report for Accession No. H47097, Aug. 16, 1995.
Hill-Perkins, Possee, J. Gen Virol., vol. 71, pp. 971-976 (1990).
Holloway, M.P. and R.J. Bram, "A Hydrophobic Domain of $Ca^{2+}$ Modulating Cyclophilin Ligand Modulates Calcium Influx Signaling in T Lymphocytes," The Journal of Biological Chemistry, vol. 271, No. 15, pp. 8549-8552 (1996).
Holloway, M.P. and R.J.Bram, "Co-localization of Calcium-modulating Cyclophilin Ligand with Intracellular Calcium Pools," Journal of Biological Chemistry, vol. 273, No. 26, pp. 16346-16350 (Jun. 26, 1992).
Holm, Nuc. Acids Res., vol. 14, pp. 3075-3087 (1986).
Hopp, Woods Proc. Nat. Acad. Sci., vol. 78, pp. 3824-3828 (1981).
Hoth, M. and R. Penner, Calcium Release-Activated Calcium Current in Rat Mast Cells, Journal of Physiology, vol. 465, pp. 359-386 (1993).
Houdebine, "Transgenic Animal Bioreactors," Transgenic Research, vol. 9, pp. 305-320 (2000).
Houdebine, L-M., 2002, Journal of Biotechnology, vol. 98, p. 145-160.
Hubbard, M.J., et al., vol. 28, pp. 1868-1874 (1989).
Idemura, J. Mol Biol., vol. 158, pp. 573-597 (1982).
Imboden, J.B., et al., "The Antigen Receptor on a Human T Cell Line Initiates Activation by Increasing Cytoplasmic Free Calcium" Journal of Immunology, vol. 134, No. 2, pp. 663-665 (Feb. 1985).
Inbar, et al., Proc. Natl. Acad. Sci., vol. 69, p. 2659 (1972).
InNEXUS Lead Candidate DXL625Outpeforms Rituxan in Additional Animal Studies, [Online] Retrieved from Scientific Blogging, XP-002515036, (2008, pp. 1-2, Presentation American Association for Cancer Research, San Diego, CA, 2008, pp. 1-14.
Interlocutory Decision in Opposition Proceedings of EP 00902354 dated Nov. 30, 2007.
International Preliminary Report on Patentability of PCT/US00/00396 dated Jun. 19, 2001.
International Preliminary Report on Patentability of PCT/US2006/031277 dated Aug. 9, 2005.
International Preliminary Report on Patentability of PCT/US2007/068982 dated Nov. 27, 2008.
International Preliminary Report on Patentability of PCT/US98/04270 dated Jan. 5, 1999.
International Search Report of PCT/US00/00396 dated Jul. 7, 2000.
International Search Report of PCT/US2008/080177 dated Feb. 26, 2009.
International Search Report of PCT/US98/04270 dated Aug. 21, 1998.
Jones, et al., Nature, vol. 321, p. 522 (1986).
Kalled, S.L., et al., "BAFF; B Cell Survival Factor and Emerging Therapeutic Target for Autoimmune Disorders," Expert Opin. Ther. Targets, vol. 7, No. 1, pp. 115-123 (2003).
Karttunen, J., and N. Shastri, "Measurement of Ligand-induced Activation in Single Viable T Cells Using the lacZ Reporter Gene," Proc. Natl. Acad. Sci. USA, vol. 88, pp. 3972-3976 (May 1991).
Khare, et al., Proc. Natl. Acad. Sci. USA, vol. 97, pp. 3370-3375 (2000).
Kohler, et al., Nature, vol. 257, p. 495 (1975).

(56) References Cited

OTHER PUBLICATIONS

Kolb, et al., Insertion of a Foreign Gene into the Beta-casein Locus by Cre-mediated Site-specific Recombination, Gene, vol. 227, pp. 21-31 (1999).
Korganow, et al., Immunity, vol. 10, pp. 451-461 (1999).
Kyte, Doolittle, J. Mol. Biol., vol. 157, pp. 105-142 (1982).
Larrick, et al., Methods: A Companion to Methods in Enzymology, vol. 2, p. 106 (1991).
Leiter, E.H. & Lee, C-H., "Is There Evidence for Genetic Overlap Between Type 1 and Type 2 Diabestes?" Diabetes, vol. 54, Supp. 2, pp. S151-S158 (2005).
Leiter, et al. "Mice with targeted gene disruptions or gene insertions for diabetes research; problems, pitfalls, and potential solutions," Diabetologia, vol. 45, pp. 296-308 (2002).
Liapakis, G., et al., "Identification of Ligand Binding Determinants in the Somatostatin Receptor Subtypes 2 and 2," Journal of Biological Chemistry, vol. 271, No. 34, pp. 20331-20339 (1996).
Lin, J.C., et al., "A Microdomain Formed by the Extracellular Ends of the Transmembrane Domains Promotes Activation of the G Protein-Coupled α-Factor Receptor," Molecular and Cellular Biology, vol. 24, No. 5, pp. 2041-2051 (2004).
Liu, J., et al., "Calcineurin is a Common Target of Cyclophilin-Cyclosporin A FKBP-FK506 Complexes," Cell, vol. 66, pp. 807-815 (Aug. 13, 1991).
Lonberg, et al., Nature, vol. 368, p. 856 (1994).
Losman, et al., Int. J. Cancer, vol. 46, p. 310 (1990).
Luckow, et al., J. Virol., vol. 67, pp. 4566-4579 (1993).
Mathey-Prevot, et al., Mol. Cell. Biol., vol. 6, pp. 4133-4135 (1986).
Merck, 17th Edition, Section 6-Pulmonary Disorders, pp. 568-569.
Miller, et al., GenBank Report for Accession No. R24371, Apr. 20, 1995.
Mishra, GenBank Report for Accession No. V64412, Mar. 1, 1999.
Neumann, et al., Embo J., vol. 1, pp. 841-845 (1982).
Nilsson, et al., Embo J., vol. 4, p. 1075, (1985).
Nilsson, et al., Methods Enzymol., vol. 198, p. 3 (1991).
Nisonoff, et al., Biochem. Biophys. Acta., vol. 89, p. 230 (1960).
Novake, Anne, J., et al., Blood, vol. 103, No. 2, pp. 689-694 (2004).
O'Keefe, S.J., et al., "FK-506 and CsA-sensitive Activation of the Interleukin-2 Promoter by Calcineurin," Nature, vol. 357, pp. 692-694 (Jun. 25, 1992).
Orlandi, et al., Proc. Natl. Acad. Sci., vol. 86, p. 3833 (1989).
Pack, et al., Bio/Technology, vol. 11, p. 1271 (1993).
Palacios, Steinemetz, Cell, vol. 41, pp. 727-734 (1985).
Perez-Melgosa, et al., J. Immunol., vol. 163, p. 1123-1127 (1999).
Porter, Biochem. J., vol. 73, p. 119 (1959).
Premack, B.A., et al., "Activation of $CA^{2+}$ Current in Jurkat T Cells Following the Depletion of $Ca^{2+}$ Stores by Microsomal $Ca^{2+}$-ATPase Inhibitors," Journal of Immunology, vol. 152, pp. 5226-5240 (1994).
Putney, J.W., Jr., and G.St. J. Bird, The Signal for Capactiative Calcium Entry, Cell, vol. 75, pp. 199-201 (Oct. 22, 1993).
Ramser, et a l., GenBank Report for Accession No. AL353996 (2000).
Raymond, et al., Yeast, vol. 14, pp. 11-23 (1998).
Roitt, I., et al., "Autoimmunity and Autoimmune Disease—27," Immunolgy, Fourth Edition, pp. 271-272 (1996).
Rudinger, J., "Characteristics of the Amino Acids as Components of Peptide Hormone Sequence," Peptide Hormones, University Park Press, Baltimore, pp. 1-7, (Jun. 1976).
Ryan, M., et al., "Antibody Targeting of B-Cell Maturaiton Antigen on Malignant Plasma Cells," Molecular Cancer Therapeutics, vol. 16, No. 11, US American Associate of Cancer Research pp. 3009-3018 (Nov. 2007).
Santee, S.M., and L.B. Owen-Schaub, "Human Tumor Necrosis Factor Receptor p75/80 (CD120B) Gene Structure and Promoter Characterization," The Journal of Biological Chemistry, vol. 271, No. 35, pp. 21151-21159 (1996).
Scatchard Ann. Ny. Acad. Sci., vol. 51, p. 660 (1949).
Sethi, S., et al., "Oxidized Omega-3 Fatty Acids in Fish Oil Inhibit Leukocyte-Endothelial Interactions Through Activation of Pparg," Blood, vol. 100, No. 4, pp. 1340-1346 (2002).
Shu, et al., J. Leukoc Biol., vol. 65, pp. 680-683 (1999).
Sigmund, C., Jun. 2000, Arterioscler. Thromb. Vasc. Biol., p. 1425-1429.
Silverman, G.J., et al., "B Cell Modulation in Rheumatology," Current Opinion in Pharmacology—Cancer/Immunomodulation 200708 GB, vol. 7, No. 4, pp. 426-433 (Aug. 4, 2007).
Singer, et al., J. Immun., vol. 150, p. 2844 (1993).
Sinkar, et al., J. Biosci., vol. 11, pp. 47-58 (1987).
Sipos, L., et al., Eur. J. Biochem., vol. 213, pp. 1333-1340 (1993).
Smith, et al., "The TNF Receptor Superfernily of Cellular and Viral Proteins" Activation, Costimulation and Death vol. 76, pp. 959-962 (1994).
Smith, Johnson, Gene, vol. 67, p. 31 (1988).
Stohl, et al., "B Cell Depletion Therapy in Systemic Rheumatic Diseases: Different Strokes for Different Folks?" Clinical Immunology, vol. 121, No. 1, pp. 1-12 (Oct. 1, 2006) (Abstract).
Stryer, L., "Flow of Genetic Information," Biochemistry Fourth Edicition, W.H. Freeman and Company, New York, pp. 111 (1996).
Stuve, O., et al., "Clinical Stabilization and Effective B-lymphocyte Depletion in the Cerebrospinal Fluid and Peripheral Blood of a Patient with Fulminant Relapsing-Remitting Multiple Sclerosis," Archives of Neurology, vol. 62, No. 10, pp. 1620-1623 (Oct. 2005).
Sulkowski, Trends in Biochem, vol. 1, p. 7 (1985).
Takashi, et al., Japanese Journal of Science, vol. 28, No. 5, pp. 333-342, (Oct. 2005) Abstract.
Takebe, Y., et al., SrαPromoter: an Efficient and Versatile Mammalian cDNA Expression System Composed of the Simian Virus 40 Early Prometer and the R-US Segment of Human T-Cell Leukemia Virus Type 1 Long Terminal Repeat, Molecular and Cellular Biology, vol. 8, No. pp. 466-472 (Jun. 1988).
Tashiro, K., et al., "Signal Sequence Trap: A Cloning Strategy for Secreted Proteins and Type I Membrane Proteins," Science, vol. 261, pp. 600-603 (Jul. 30, 1993).
Taylor, et al., Int. Immun., vol. 6, p. 579 (1994).
Truneh, A., et al., Early Steps of Lymphocyte Activation Bypassed by Synergy Between Calcium Ionophores and Phorbol Ester, Nature, vol. 313, pp. 318-320 (Jan. 24, 1985).
Tuan, et al., Connect Tiss. Res., vol. 34, pp. 1-9 (1996).
Varthakavi, Minocha, J. Gen. Virol., vol. 77, p. 1875 (1996).
Verweij, C.L., et al., "Cell Type Specificity and Activation Requirements for NFAT-1 (Nuclear Factor of Activated T-cells) Transcriptional Activity Determined by a New Method Using Transgenic Mice to Assay Transcriptional Activity of an Individual Nuclear Factor," Journal of Biological Chemistry, vol. 265, No. 26, pp. 15788-15795 (Sep. 15, 1990).
Von Bulow and R.J. Bram, "Activation of the Transcription Factor NFAT by a Novel CAML-Interacting Member of the Tumor Necrosis Factor Receptor Superfamily," Blood, vol. 90, No. 10, Suppl. 1, Part 1, pp. 246A-247 (1997).
Von Bulow, G.U., et al., "Molecular Cloning and Functional Characterization of Murine Transmembrane Activator and CAML Interactor (TACI) with Chromosomal Localization in Human and Mouse," Mammalian Genome, vol. 11, pp. 628-632 (2000).
Vugmeyster, Y., et al., "A Soluble BAFF Antagonist, BR3-Fc, Decreases Peripheral Blood B Cells and Lymphoid Tissue Marginal Zone and Follicular B Cells in Cynomolgus Monkeys," American Journal of Pathology 200602 US, vol. 168, No. 2, pp. 476-489 (Feb. 2, 2006).
Wada, A., et al., "Identification of Ligand Recognition Sites in Heat-Stable Enterotoxin Receptor, Membrane-Associated Guanylyl Cyclase C by Site-Directed Mutational Analysis," Infection and Immunity, vol. 64, No. 12, pp. 5144-5150 (1996).
Wain-Hobson, et al., Gene, vol. 13, pp. 355-364 (1981).
Ware, Nature, vol. 404, pp. 949-950 (2000).
Weiss, A., and D.R. Littman, et al., "Signal Transduction by Lymphocyte Antigen Receptors," Cell, vol. 76, pp. 263-274 (Jan. 28, 1994).
Wigler, et al., Cell, vol. 14, p. 7 25 (1978).
Wilson-Rawls, J., et al., Virology, vol. 201, pp. 66-76 (1994).
Wu, Y., et al., Tumor Necrosis Factor (TNF) Receptor Superfamily Member TACI is a High Affinity Receptor for TNF Family Members APRIL and BLyS, The Journal of Biological Chemistry, vol. 275, No. 45, pp. 35478-35485 (2000).

(56) References Cited

OTHER PUBLICATIONS

Yan, et al., Nature Immunol., vol. 1, pp. 37-41 (2000).
Yang, M., et al., "B Cell Maturation Antigen, the Receptor for a Proliferation-Inducing Ligand and B Cell-Activating Factor of the TNF Family, Induces Antigen Presentation in B Cells," Journal of Immunology, vol. 175, US The Williams and Wilkins Co., Baltimore, pp. 2814-2824 (Sep. 2005).
Yu, G., et al., "April and TALL-I and Receptors BCMA and TACI: System for Regulating Humoral Immunity," Nature, vol. 1, No. 3, pp. 252-256 (2000).
Zhou, et al., Blood, vol. 98, No. 11:808a, Abstract 3361 (2001).
Zhu, J., et al., "Plasma Cells and IL-4 in Chronic Bronchitis and Chronic Obstructive Pulmonary Disease," American Journal of Respiratory and Critical Care Medicine, vol. 175, US American Lung Association, New York, NY vol. 175, pp. 1125-1133 (Jun. 2007).
Zweifach, A., and R.S. Lewis, "Mitogen-regulated $CA^{2+}$ Current of T Lymphocytes is Activated by Depletion of Intracellular $CA^{2+}$ Stores," Proc. Natl. Acad. Sci. USA, vol. 90, pp. 6295-6299 (Jul. 1993).
U.S. Appl. No. 11/748,978 Final office action dated Jun. 12, 2009.
U.S. Appl. No. 09/479,856 Restriction Requirement dated Jul. 28, 2000.
U.S. Appl. No. 09/627,206 Restriction Requirement dated Sep. 7, 2001.
U.S. Appl. No. 09/627,206 Restriction Requirement dated Apr. 26, 2002.
U.S. Appl. No. 09/627,206 Non-final office action dated Aug. 8, 2002.
U.S. Appl. No. 09/627,206 Final Office Action dated Apr. 28, 2003.
U.S. Appl. No. 09/627,206 Advisory Action dated Mar. 3, 2004.
U.S. Appl. No. 09/627,206 Non-final Office action dated Aug. 6, 2004.
U.S. Appl. No. 09/627,206 Final Office action dated May 23, 2005.
U.S. Appl. No. 09/627,206 Non-final Office action dated Dec. 29, 2006.
U.S. Appl. No. 09/627,206 Non-final Office Action Dec. 7, 2007.
U.S. Appl. No. 09/627,206 Final Office Action dated Aug. 18, 2008.
U.S. Appl. No. 09/627,206 Non-final office action dated Feb. 11, 2009.
U.S. Appl. No. 11/200,992 Non-Final Office Action dated Mar. 21, 2008.
U.S. Appl. No. 11/200,992 Final Office Action dated Dec. 15, 2008.
U.S. Appl. No. 11/242,294 Non-Final office action dated Jun. 22, 2007.
U.S. Appl. No. 11/242,294 Final Office Action dated May 28, 2008.
U.S. Appl. No. 11/242,294 Notice of Allowance dated Oct. 24, 2008.
U.S. Appl. No. 12/057,133 Restriction Requirement dated Jul. 13, 2009.
U.S. Appl. No. 10/152,363 Restriction Requirement dated Oct. 31, 2003.
U.S. Appl. No. 10/152,363 Non-final office action dated Feb. 24, 2004.
U.S. Appl. No. 10/152,363 Final office action dated Apr. 1, 2005.
U.S. Appl. No. 09/569,245 Restriction Requirement dated Sep. 7, 2001.
U.S. Appl. No. 09/569,245 Restriction Requirement dated Apr. 10, 2002.
U.S. Appl. No. 09/569,245 Non-Final Office Action dated Aug. 8, 2002.
U.S. Appl. No. 09/569,245 Final Office Action dated Apr. 25, 2003.
U.S. Appl. No. 09/569,245 Advisory Action dated Mar. 9, 2004.
U.S. Appl. No. 09/569,245 Non-Final Office Action dated Aug. 6, 2004.
U.S. Appl. No. 09/569,245 Final office Action dated May 23, 2005.
U.S. Appl. No. 09/569,245 Non-Final Office Action dated Sep. 12, 2006.
U.S. Appl. No. 09/569,245 Non-Final Office Action dated Nov. 16, 2007.
U.S. Appl. No. 09/569,245 Final Office Ation dated Aug. 21, 2008.
U.S. Appl. No. 09/569,245 Non-Final Office Action dated Feb. 13, 2009.
U.S. Appl. No. 12/252,955 Restriction Requirement dated Sep. 4, 2009.
U.S. Appl. No. 12/359,801 Notice of Allowance dated Aug. 17, 2009.
Berenbaum, "Synergy, Additivism and Antagonism in Immunosuppression," Clin. Exp. Immunol., vol. 28, pp. 1-18 (1977).
Bilsborough, J., et al., "TACI-Ig Prevents the Development of Airway Hyper-Responsiveness in a Murine Model of Asthma," Clinical & Experimental Allergy, vol. 38, No. 12, pp. 1959-1968 (2008).
Dooley, M., et al., "Mycophenolate Mofetil Therapy in Lupus Nephritis: Clinical Observations," J. Am. Soc. Nephroi., vol. 10, pp. 833-839 (1999).
Jonsson., et al., "Mycophenolic Acid Inhibits Inosine 5'-Monophosphate Dehydrogenase and Suppresses Immunoglobulin and Cytokine Production of B Cells," International Immunopharmacology, vol. 3, pp. 31-37 (2003).
Koyama, et al., "Raised Serum APRIL Levels in Patients with Systemic Lupus Erythematosus," Ann Rheum. Dis., vol. 64, pp. 1065-1067 (2005).
Lee, H. J., "Protein Drug Oral Delivery: The Recent Progres," Arch. Pharm. Res., vol. 25, No. 5, pp. 572-584 (2002).
Pena-Rossi, C., et al., "An Exploratory Dose-Escalating Study Investigating the Safety, Tolerability, Pharmacokinetics and Pharmacodynamics of Intravenous Atacicept in Patients with Systemic Lupus Erythematosus," Lupus, vol. 18, No. 6, pp. 547-555 (2009).
Stein, et al., "APRIL Modulates B and T Cell Immunity," J. Clin. Invest., vol. 109, pp. 1587-1598 (2002).
Stohl, W., et al., "B Lymphocyte Stimulator Protein-Associated Increase in Circulating Autoantibody Levels May Require CD4+ T Cells: Lessons from HIV-Infected Patients," Clinical Immunology, vol. 104, No. 2, pp. 115-122 (2002).
Tak, P. P., et al., "Atacicept in Patients with Rheumatoid Arthirits: A, Multi-Center, double- Blind, Placebo-Controlled, Dose-Escalating, Single and Repeat Dose Study," Arthritis Rheum., vol. 58, No. 1, pp. 61-72 (2008).
U.S. Appl. No. 09/627,206 Final office action dated Oct. 27, 2009.
U.S. Appl. No. 11/748,978 Non-final office action dated Dec. 4, 2009.
U.S. Appl. No. 11/502,134 Non-final office action dated Dec. 2, 2009.
U.S. Appl. No. 11/458,968 Restriction Requirement dated Mar. 23, 2009.
U.S. Appl. No. 11/458,968 Non-Final Office Action dated Jun. 24, 2009.
U.S. Appl. No. 11/458,968 Notice of Allowance dated Dec. 16, 2009.
U.S. Appl. No. 12/057,133 Non-Final Office Action dated Feb. 4, 2010.
Ansel, Stephen M ., et al., B-Lymphocyte Stimulator (BLyS) Is Highly Expressed in Waldenstrom's Macroglobulinemia, Blood, (ASH Annual Meeting Abstracts), vol. 104, p. 917A, Abstract 2291 (2004).
Santos, Daniel D., et al., "B-Lymphocyte Stimulator Protein (BLYS) Is Expressed by Bone Marrow Mast and Lymphoplasmacytic Cells in Waldenstrom's Macroglobulinemia and Provides Signaling for Growth, Survival and IgM Secretion," Blood (ASH Annual Meeting Abstracts), vol. 104, p. 630A, Abstract 3358 (2004).
U.S. Appl. No. 11/748,978 Examiner's Answer dated Mar. 29, 2011.
U.S. Appl. No. 11/502,134 Notice of Allowance dated Jul. 23, 2010.
U.S. Appl. No. 11/502,134 Final Office Action dated May 27, 2010.
U.S. Appl. No. 11/748,978 Final Office Action dated Jun. 9, 2010.
U.S. Appl. No. 09/627,206 Advisory Action dated Mar. 5, 2010.
U.S. Appl. No. 09/627,206 Advisory Action dated Mar. 25, 2010.
U.S. Appl. No. 09/627,206 Notice of Allowance dated Jul. 8, 2010.
U.S. Appl. No. 09/569,245 Final Office Action dated Nov. 17, 2009.
U.S. Appl. No. 09/569,245 Advisory Action dated Mar. 11, 2010.
U.S. Appl. No. 12/057,133 Final Office Action dated Aug. 17, 2010.
U.S. Appl. No. 12/057,133 Examiner Interview Summary dated Jan. 27, 2011.
U.S. Appl. No. 12/952,048 Restriction requirement dated May 12, 2011.
Ansell, et al., Clin. Cancer Res., vol. 14, No. 4, pp. 1105-1110 (Feb. 15, 2008).

(56) References Cited

OTHER PUBLICATIONS

International Preliminary Report on Patentability of PCT/US2008/080177 dated Apr. 20, 2010.
Nestorov, I., et al., Pharmacokinetics and Biological Activity of Atacicept in Patients with Rheumatoid Arthritis, The Journal of Clinlical Pharmacology, vol. 48, p. 406-417 (2008).
Rossi, J., et al., "Atacicept in Relapsed/Refractory Multiple Myeloma or Active Waldenstrom's Macroglobulinemia: A Phase I Study" British Journal of Cancer, vol. 101, pp. 1051-1058 (2009).
Tak, P. P., et al., "Atacicept in Patients with Rheumatoid Arthirits: Resi;ts pf a Multicenter, Double- Blind, Placebo-Controlled, Dose-Escalating, Single- and Repeated-Dose Study," Arthritis Rheum., vol. 58, No. 1, pp. 61-72 (2008).
U.S. Appl. No. 12/952,048—Non-Final office action dated Sep. 23, 2011.
U.S. Appl. No. 12/952,048—Advisory Action dated May 31, 2012.
U.S. Appl. No. 12/952,048—Final office action dated Mar. 13, 2012.
U.S. Appl. No. 12/952,048—Non-final office action dated Nov. 4, 2013.
U.S. Appl. No. 12/905,971 Non-final office action dated May 19, 2011.
U.S. Appl. No. 12/905,971 Final Office Action dated Oct. 17, 2011.
U.S. Appl. No. 12/905,971—Non-final office action dated Sep. 13, 2013.
U.S. Appl. No. 12/905,971—Final office action dated Mar. 3, 2014.
U.S. Appl. No. 12/605,561—Restriction Requirement dated Jul. 13, 2010.
U.S. Appl. No. 12/605,561—Non-final office action dated Sep. 17, 2010.
U.S. Appl. No. 12/605,561—Notice of Allowance dated Feb. 24, 2011.
U.S. Appl. No. 12/612,288—Non-final office action dated Jul. 22, 2010.
U.S. Appl. No. 12/612,288—Notice of Allowance dated Dec. 23, 2010.
U.S. Appl. No. 12/613,039—Notice of Allowance dated Aug. 25, 2010.
U.S. Appl. No. 13/105,182—Restriction Requirement dated Oct. 31, 2011.
U.S. Appl. No. 13/105,182—Non-final office action—Apr. 10, 2012.
U.S. Appl. No. 13/105,182—Ex Parte Quayle Action dated Dec. 4, 2012.
U.S. Appl. No. 13/105,182—Notice of Allowance dated May 7, 2013.
U.S. Appl. No. 13/956,499—Restriction Requirement dated Sep. 19, 2013.
U.S. Appl. No. 13/956,499—Non-final office action dated Dec. 11, 2013.
Ginzler, et al., "Atacicept in Combination with MMF and Corticosteroids in Lupus Nephritis: Results of a Prematurely Terminated Trial," Arthritis Research & Therapy, vol. 14, R33, pp. 1-7 (2012).
Martineau, P., et al., "Expression of an Antibody Fragment at High Levels in the Bacterial Cytoplasm," J. Mol. Biol., vol. 280, pp. 117-127 (1998).
European Search Report of EP 10175468.7 dated Oct. 20, 2010.

\* cited by examiner

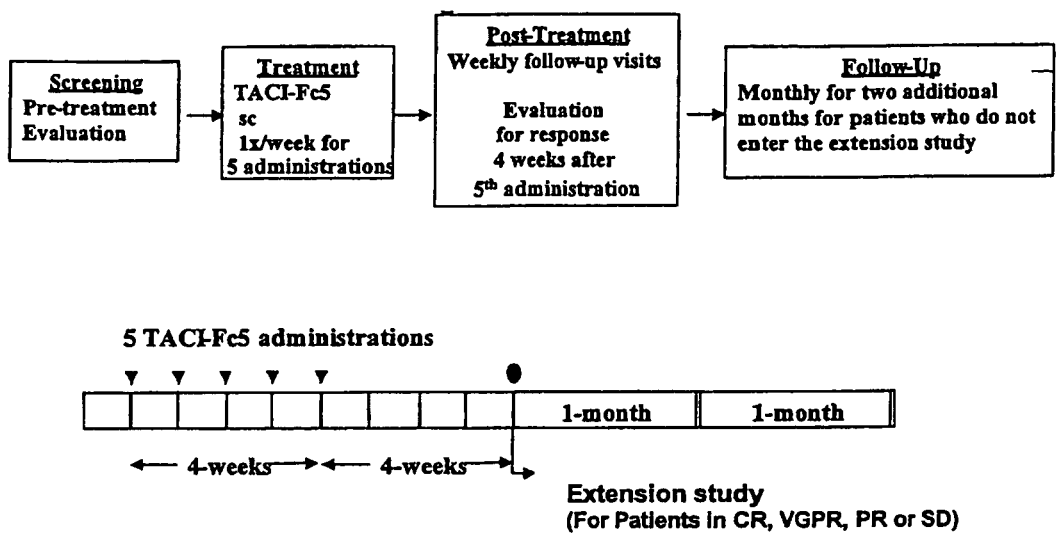
Figure 1: Study overview of the first part

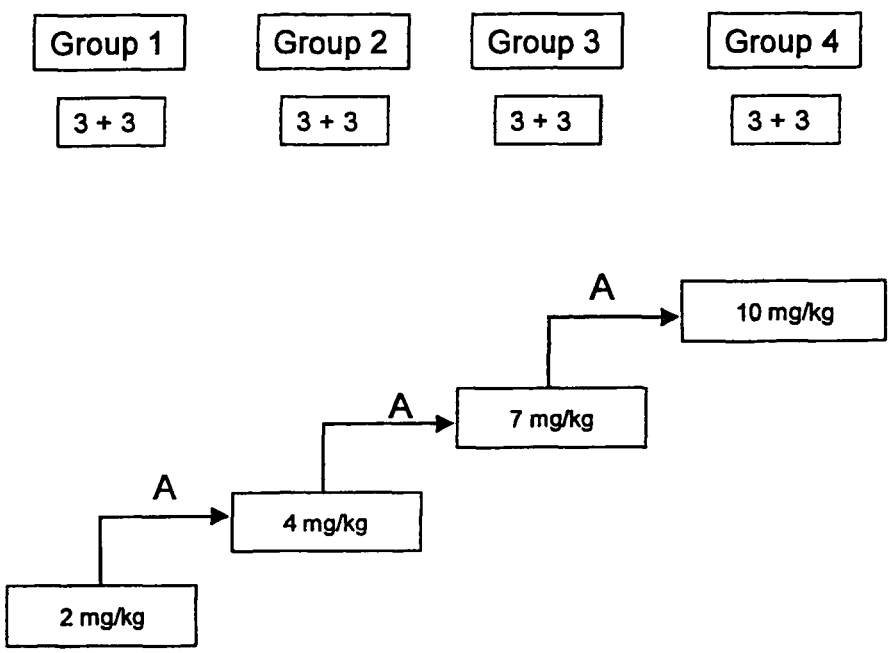
Figure 2: Dose-escalation scheme of the first part of the study

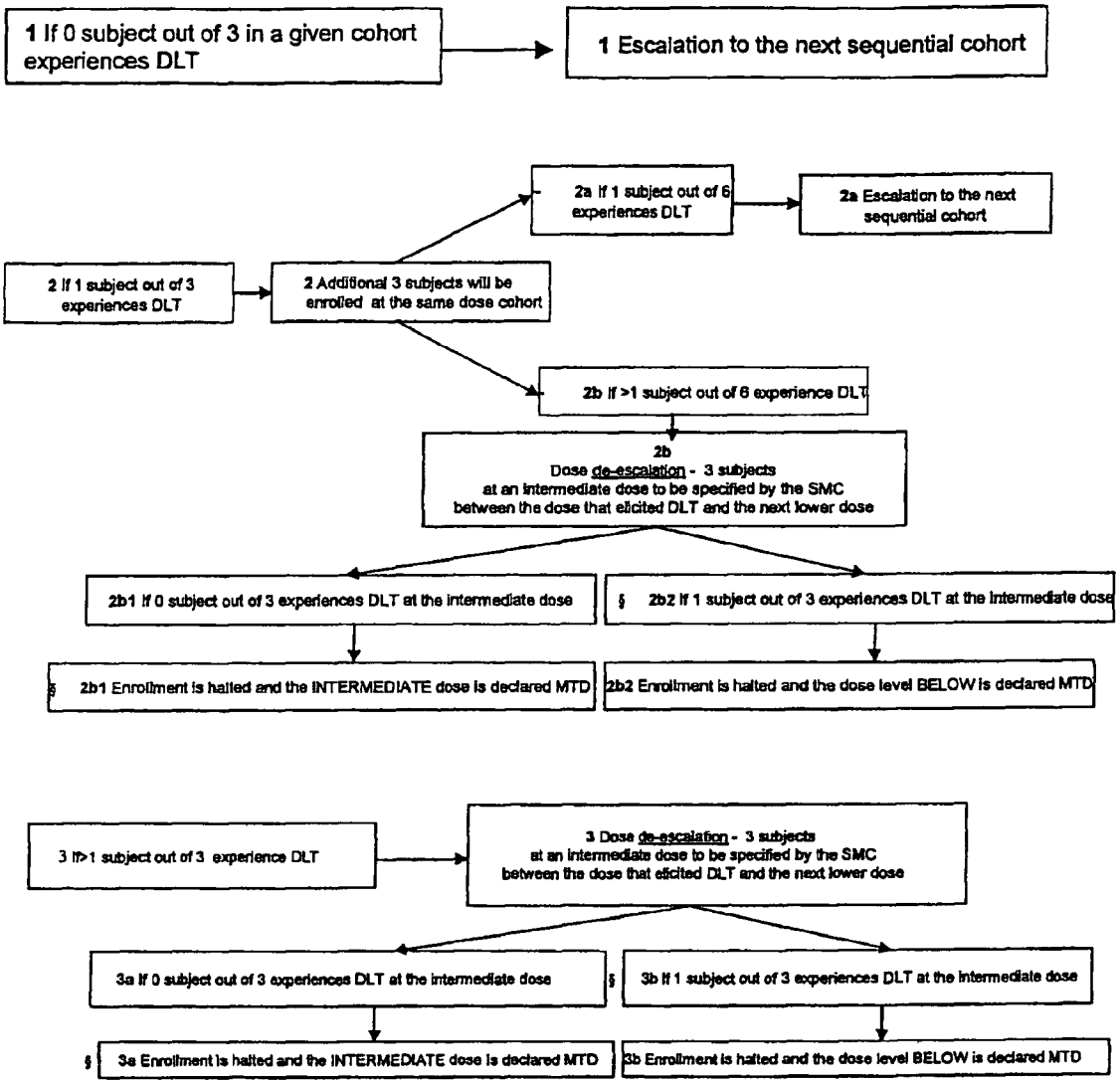
Figure 3: Dose-escalation decision tree- 3+3 design

Figure 4: Study overview of the second part
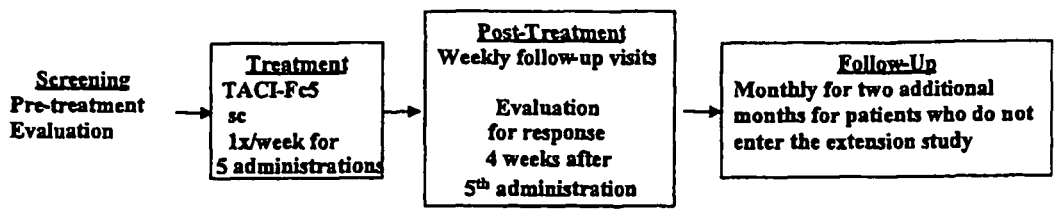
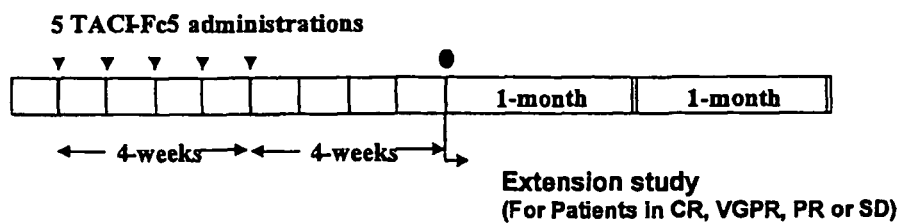
Extension study
(For Patients in CR, VGPR, PR or SD)

The possible zones for injection are (see figure below):
1. right upper external area
2. left lower external area
3. right lower external area
4. left upper external area
5. median lower area

Figure 7: SEQ ID NO. 1

```
Met Ser Gly Leu Gly Arg Ser Arg Arg Gly Gly Arg Ser Arg Val Asp
1               5                   10                  15
Gln Glu Glu Arg Phe Pro Gln Gly Leu Trp Thr Gly Val Ala Met Arg
            20                  25                  30
Ser Cys Pro Glu Glu Gln Tyr Trp Asp Pro Leu Leu Gly Thr Cys Met
            35                  40                  45
Ser Cys Lys Thr Ile Cys Asn His Gln Ser Gln Arg Thr Cys Ala Ala
    50                  55                  60
Phe Cys Arg Ser Leu Ser Cys Arg Lys Glu Gln Gly Lys Phe Tyr Asp
65                  70                  75                  80
His Leu Leu Arg Asp Cys Ile Ser Cys Ala Ser Ile Cys Gly Gln His
            85                  90                  95
Pro Lys Gln Cys Ala Tyr Phe Cys Glu Asn Lys Leu Arg Ser Pro Val
            100                 105                 110
Asn Leu Pro Pro Glu Leu Arg Arg Gln Arg Ser Gly Glu Val Glu Asn
        115                 120                 125
Asn Ser Asp Asn Ser Gly Arg Tyr Gln Gly Leu Glu His Arg Gly Ser
    130                 135                 140
Glu Ala Ser Pro Ala Leu Pro Gly Leu Lys
145                 150
```

Figure 8: SEQ ID NO. 2

Met Asp Ala Met Lys Arg Gly Leu Cys Cys Val Leu Leu Leu Cys Gly
1               5                       10                      15
Ala Val Phe Val Ser Leu Ser Gln Glu Ile His Ala Glu Leu Arg Arg
                20                      25                      30
Phe Arg Arg Ala Met Arg Ser Cys Pro Glu Glu Gln Tyr Trp Asp Pro
            35                      40                      45
Leu Leu Gly Thr Cys Met Ser Cys Lys Thr Ile Cys Asn His Gln Ser
        50                      55                      60
Gln Arg Thr Cys Ala Ala Phe Cys Arg Ser Leu Ser Cys Arg Lys Glu
65                      70                      75                      80
Gln Gly Lys Phe Tyr Asp His Leu Leu Arg Asp Cys Ile Ser Cys Ala
                85                      90                      95
Ser Ile Cys Gly Gln His Pro Lys Gln Cys Ala Tyr Phe Cys Glu Asn
                100                     105                     110
Lys Leu Arg Ser Glu Pro Lys Ser Ser Asp Lys Thr His Thr Cys Pro
            115                     120                     125
Pro Cys Pro Ala Pro Glu Ala Glu Gly Ala Pro Ser Val Phe Leu Phe
    130                     135                     140
Pro Pro Lys Pro Lys Asp Thr Leu Met Ile Ser Arg Thr Pro Glu Val
145                     150                     155                     160
Thr Cys Val Val Val Asp Val Ser His Glu Asp Pro Glu Val Lys Phe
                165                     170                     175
Asn Trp Tyr Val Asp Gly Val Glu Val His Asn Ala Lys Thr Lys Pro
                180                     185                     190
Arg Glu Glu Gln Tyr Asn Ser Thr Tyr Arg Val Val Ser Val Leu Thr
        195                     200                     205
Val Leu His Gln Asp Trp Leu Asn Gly Lys Glu Tyr Lys Cys Lys Val
        210                     215                     220
Ser Asn Lys Ala Leu Pro Ser Ser Ile Glu Lys Thr Ile Ser Lys Ala
225                     230                     235                     240
Lys Gly Gln Pro Arg Glu Pro Gln Val Tyr Thr Leu Pro Pro Ser Arg
                245                     250                     255
Asp Glu Leu Thr Lys Asn Gln Val Ser Leu Thr Cys Leu Val Lys Gly
            260                     265                     270
Phe Tyr Pro Ser Asp Ile Ala Val Glu Trp Glu Ser Asn Gly Gln Pro
        275                     280                     285
Glu Asn Asn Tyr Lys Thr Thr Pro Pro Val Leu Asp Ser Asp Gly Ser
    290                     295                     300
Phe Phe Leu Tyr Ser Lys Leu Thr Val Asp Lys Ser Arg Trp Gln Gln
305                     310                     315                     320
Gly Asn Val Phe Ser Cys Ser Val Met His Glu Ala Leu His Asn His
                325                     330                     335
Tyr Thr Gln Lys Ser Leu Ser Leu Ser Pro Gly Lys
            340                     345

METHODS FOR THE TREATMENT AND PREVENTION OF ABNORMAL CELL PROLIFERATION USING TACI-FUSION MOLECULES

CROSS-REFERENCE TO RELATED APPLICATIONS

This application claims the benefit of U.S. Provisional Application No. 60/706,888, filed Aug. 9, 2005, the contents of which are incorporated herein by reference.
Sequence Listing Submission via EFS-Web.

A computer readable text file, entitled "Serono-31-Substitute-Sequence-Listing ST.25.txt," created on or about Jan. 4, 2011, with a file size of about 5 KB, contains the sequence listing for this application and is hereby incorporated by reference in its entirety.

FIELD OF THE INVENTION

The present invention relates to methods and compositions for the treatment of diseases and disorders, including hyperproliferative disorders, cancer, inflammatory diseases or disorders and diseases of the immune system, comprising administering a TACI-Ig fusion protein which blocks functions of growth factors of the TNF family.

BACKGROUND OF THE INVENTION

The BlyS Ligand/Receptor Family

Three receptors, TACI (transmembrane activator or CAML-interactor), BCMA (B-cell maturation antigen) and BAFF-R (receptor for B-cell activating factor, belonging to the TNF family), have been identified that have unique binding affinities for the two growth factors BlyS (B-lymphocyte stimulator) and APRIL (a proliferation-inducing ligand) (Marsters et al. Curr Biol 2000; 10(13):785-788; Thompson et al. Science 2001; 293-21 08-2111). TACI and BCMA bind both BLyS and APRIL, while BAFF-R appears capable of binding only BLyS with high affinity (Marsters et al. Curr Biol 2000; 10(13):785-788; Thompson et al. Science 2001; 293:2108-2111). As a result, BLyS is able to signal through all three receptors, while APRIL only appears capable of signaling through TACI and BCMA. In addition, circulating heterotrimer complexes of BLyS and APRIL (groupings of three proteins, containing one or two copies each of BLyS and APRIL) have been identified in serum samples taken from patients with systemic immune-based rheumatic diseases, and have been shown to induce B-cell proliferation in vitro (Roschke et al. J Immunol 2002; 169:4314-4321).

BLyS and APRIL are potent stimulators of B-cell maturation, proliferation and survival (Moore et al. Science 1999; 285(5425): 260-263; Schneider et al. J Exp Med 1999; 189 (11): 1747-1756; Do et al. J Exp Med 2000; 192(7):953-964). BLyS and APRIL may be necessary for persistence of autoimmune diseases, especially those involving B-cells. Transgenic mice engineered to express high levels of BLyS exhibit immune cell disorders and display symptoms similar to those seen in patients with Systemic Lupus Erythematosus (Gross et al. Nature 2000; 404:995-999; Mackay et al. J Exp Me 1999; 190(11); 1697-1710). Similarly, increased levels of BLyS/APRIL have been measured in serum samples taken from Systemic Lupus Erythematosus patients and other patients with various autoimmune diseases like Rheumatoid Arthritis (Roschke et al. J Immunol 2002; 169:4314-4321; Cheema et al. Arthritis Rheum 2001; 44(6): 1313-1319; Groom et al. J Clin Invest 2002; 109(1):59-68; Mariette X, Ann Rheum Dis 2003; 62(2):168-171), extending the association of BLyS and/or APRIL and B-cell mediated diseases from animal models to humans.

Multiple Myeloma

Multiple myeloma (MM) is a plasma cell neoplasm characterized by the accumulation of monoclonal plasma cells in the bone marrow, associated with the synthesis of a monoclonal immunoglobulin and a high incidence of osteolytic bone lesions. Overgrowth of MM cells usually leads to immunodeficiency and destruction of the bone cortex at multiple tumor sites. Although traditionally, MM is a disease of the elderly, it is increasingly being detected in younger patients. Diagnosed patients generally have a short life expectancy. The median survival of patients treated with conventional chemotherapy is about 42 months. The use of high-dose therapy with autologous stem cell transplantation increases the median survival to 60 months in younger patients. However, the disease remains incurable.

The cause of multiple myeloma is unknown. There are approximately 74,000 new cases of MM each year worldwide, with an overall incidence of 4.5 per 100,000 per year in most Western industrialized countries. Male to female ratio is 3 to 2 and the incidence is about 2-fold higher in American blacks than in Caucasians. The median age of diagnosis is 68 years. MM accounts for 1% of all malignancies.

Osteolytic lesions, anemia, renal insufficiency and recurrent bacterial infections are the most common clinical features of multiple myeloma. All these complications, especially infections and renal insufficiency are also major causes of death. The pathogenesis of these clinical features depends on the interactions between the myeloma cells and the microenvironment of the bone marrow, by means of cell-to-cell contact, adhesion molecules and cytokines or on the direct effects of circulating monoclonal immunoglobulins or light chains. The M-protein is a hallmark of the disease. The M-protein is an overproduced homogenous immunoglobulin or immunoglobulin fragment. Monoclonal protein is used to calculate myeloma tumor burden and kinetics, to stage myeloma patients and to document their response to treatment. The different immunologic subtypes of MM are: IgG (approximately 55% of cases), 19A (approximately 26% of cases), Bence-Jones or free light chain only (approximately 14% of cases) and IgD (2% of cases). Non-secretory myeloma accounts for 1 to 5% of myeloma cases and IgM, IgE or bi-clonal MM are extremely rare. Serum beta-2 microglobulin levels, C-reactive protein levels, serum albumin levels, plasma cell labeling index (PCLI) and the presence of chromosome 13 abnormalities are prognostic factors for multiple myeloma.

The bifunctional alkylating agents like melphalan and cyclophosphamide, have been the foundation of standard therapy in multiple myeloma; the classic combination of melphalan and prednisone is still the standard treatment for most patients (Durie et al. Hematol J 2004; 4:379-398).

The regimen vincristine, doxorubicin and dexamethasone (VAD) or VAD-like regimens are commonly used as induction therapy pre-stem cell collection and transplantation. An alternative therapy is dexamethasone alone or, more recently thalidomide/dexamethasone. Indeed, thalidomide has recently been recognized as an effective agent alone or in combination for patients with MM at various stages of disease (Barlogie et al. Blood 2001; 98:492-494).

High-dose chemotherapy supported by autologous peripheral blood stem cell (PBSC)-transplantation has been accepted as an important treatment modality for patients younger than age 65. Furthermore, the approach of tandem (double) autologous stem cell transplantation is also pursued to attempt to improve Complete Response rates and survival, especially in patients who do not have a Very Good Partial Response after undergoing one transplantation. Autologous stem cell transplantation is now a safe procedure, however, contamination of the autologous graft by myeloma cells remains a concern. Maintenance treatment after transplantation with corticosteroids or IFN-alpha is often prescribed to delay relapse.

Allogeneic transplantation eliminates the problem of tumor cell contamination of the stem cells. Furthermore, there is evidence of graft-versus-myeloma effect with allografting. Standard myeloablative allogeneic transplantation can lead to prolonged disease-free survival in a small percentage of patients, but the high treatment-related mortality and significant toxicity from graft-versus-host disease have limited the role of this procedure in the treatment of myeloma. Positive results have been reported using non-myeloablative regimens (mini-allotransplants) which elicit lower acute toxicity.

The proteasome inhibitor Velcade™ (bortezomib) represents a new class of agents with activity in myeloma that is refractory to multiple lines of standard and high-dose regimen. A 35% overall response rate was reported in the pivotal phase II trial, with a 12 months median duration of response (Richardson et al. N Eng J Med 2003; 348(26):26092617). Furthermore, experimental therapies under investigation for multiple myeloma include thalidomide derivatives, vaccination, monoclonal antibodies and anti-sense drugs. Supportive therapies address the symptoms and complications of the disease. Supportive therapies commonly used in MM include bisphosphonates, growth factors, antibiotics, intravenous immunoglobulin, plasmapheresis and pain control measures. Therefore, there is a long-felt need in the field to develop effective methods for treating or ameliorating multiple myeloma.

Waldenström's Macroglobulinemia

Waldenstrom's macroglobulinemia (WM) is a condition related to MM and is the result of proliferation of lymphocytes and plasma cells which produce monoclonal IgM. The median age at presentation is 63 years and over 60% of patients are male. Many of the clinical features are the result of hyperviscosity of blood due to the raised IgM concentration. WM is characterized by hypersecretion of IgM in the serum; excess lymphoplasmacytoid cells in the bone marrow and involvement of visceral organs including liver and spleen. Primary treatment for patients who require systemic therapy includes alkylating agents or nucleoside analogs, such as cladribine and fludarabine. Steroids can be used alone or in combination with alkylating agents. Plasmapheresis is indicated for treatment of symptomatic hyperviscosity. At present there is no cure for WM patients. Therefore, there is a long-felt need in the field to develop new methods for treating or ameliorating WM.

SUMMARY OF THE INVENTION

The invention includes methods of treating or ameliorating cancer or immunological disorders, including multiple myeloma and Waldenström's macroglobulinemia. In the methods, a patient is administered an effective amount of a composition comprising a fusion polypeptide molecule, TACI-Ig, comprising a human immunoglobulin constant chain and TACI extracellular domain or a fragment thereof that binds BlyS and/or APRIL.

Methods of the invention also comprise administering to a multiple myeloma or Waldenström's macroglobulinemia patient a fusion molecule comprising a human immunoglobulin-constant domain and a polypeptide with SEQ ID NO: 1. The methods of the invention also comprise administering to a multiple myeloma or Waldenström's macroglobulinemia patient a fusion molecule comprising a human immunoglobulin-constant domain and a polypeptide which binds BlyS and/or APRIL and which is at least 50% identical to SEQ ID NO: 1, and preferably 60%, 65%, 70%, 75%, 80%, 85%, 90%, 95% or 99% identical to SEQ ID NO: 1.

In one embodiment, the methods of the invention comprise administering to a multiple myeloma or Waldenström's macroglobulinemia patient a fusion molecule comprising a human immunoglobulin-constant domain with SEQ ID NO: 2, Fc5, and a polypeptide with SEQ ID NO: 1. In another embodiment, the methods include administering to a multiple myeloma or Waldenström's macroglobulinemia patient a fusion molecule comprising a human immunoglobulin-constant domain with SEQ ID NO: 2 and a polypeptide which binds BlyS and/or APRIL and which is at least 50% identical to SEQ ID NO: 1, and preferably 60%, 65%, 70%, 75%, 80%, 85%, 90%, 95% or 99% identical to SEQ ID NO: 1.

The methods of the invention also comprise administering to a patient TACI-Ig in an amount from 0.01 mg per 1 kg of patient's body weight to 10 mg per 1 kg of patient's body weight at multiple intervals, preferably 5 times during a four-week interval, following by 4 weeks of monitoring the patient for changes in markers that are correlative with patient's disease stabilization or improvement. The correlative changes include, but are not limited to, one or more of the following: decrease of immunoglobulin IgA, IgG, IgM or IgD free light chain in patient's blood sample; decrease of M-protein (as determined by immunofixation) in patient's blood sample; decrease of M-protein (as determined by electrophoresis) in patient's blood sample; decrease of LDH, soluble syndecan-1 or beta-2 microglobulin in patient's blood sample; decrease in patient's lymphocyte cell count as determined by flow cytometry; decrease of Bence-Jones protein (as detected by immunofixation or electrophoresis) in patient's urine sample; decrease of percentage of plasma cells or lymphocyte cells, PCLI, Ki-67 or BlyS/APRIL receptors in patient's bone marrow sample. Patients whose condition is stabilized or improved by the end of the first treatment cycle, can be subjected to at least two more cycles of treatment with a TACI-Ig fusion molecule.

When used in the methods of the invention, a TACI-Ig can be administered intravenously, orally or subcutaneously. When administered subcutaneously, a TACI-Ig fusion molecule is preferably administered into any of the following areas of the anterior abdominal wall: right upper external area, left lower external area, right lower external area, left upper external area or median lower area.

The methods of the invention also include methods in which a TACI-Ig is administered to a patient in combination with other medications or methods of treatment. Such other medications include, but are not limited to, bisphosphonate, erythropoietin, granulocyte growth factors, granulocyte colony stimulating factor, drugs for the management of pain, melphalan, vincristine, doxorubicin, thalidomide, nucleoside analogs and proteosome inhibitors, including but not limited to bortezomib. Such other methods of treatment include, but are not limited to, other chemotherapeutical agents, radiotherapy and gene therapy. According to the methods of the invention, a TACI-Ig can be administered either prior, simultaneously or after a patient is subjected to other methods of treatment.

In one embodiment of the invention TACI-Ig is given in combination with bortezomib. TACI-Ig is dosed as above and bortezomib is given at a dose of $1.3 \text{ mg/m}^2$ twice weekly for two weeks, followed by a rest period of ten days. This is one cycle of treament. Preferably bortezomib is given intravenously. The response to treatment is monitored as described above for TACI-Ig alone, and additional treatment cycles of TACI-Ig and or bortezomib may be administered. TACI-Ig may be administered at a dose as described above or at a lower dose in combination with bortezomib at a dose as described or at a lower dose of bortezomib. Doses of TACI-Ig and bortezomib may be given concurrently or in alternating doses of TACI-Ig followed by a cycle of bortezomib or a cycle of bortezomib followed by a cycle of TACI-Ig. This dosing may be repeated.

TACI-Ig may be administed to those patients who have become resistant to or who do not respond to other methods of treatment, including but not limited to treatment with bortezomib.

These and other embodiments of the present invention are described in further detail herein below.

BRIEF DESCRIPTION OF THE DRAWINGS

FIG. 1. Schedule for TACI-Fc5 treatment.

FIG. 2. Dose-escalation scheme for TACI-Ig treatment.

FIG. 3. Dose-escalation decision tree of 3+3 design for TACI-Ig treatment.

FIG. 4. Outline of further treatment for patients with initial beneficial response to TACI-Ig treatment.

FIG. 7. SEQ ID NO: 1.

FIG. 8. SEQ ID NO: 2.

DETAILED DESCRIPTION OF THE INVENTION

Figure 5:
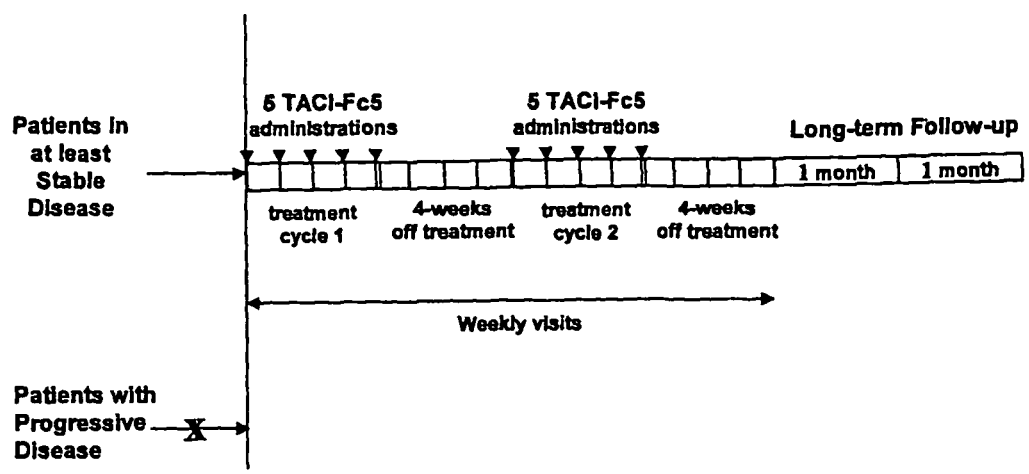
FIG. 5. Schedule of further TACI-Ig treatment for patients with initial beneficial response to TACI-Ig.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the art of pharmaceutical sciences or the art relevant to the range or element at issue. Also, the disclosure of ranges is intended as a continuous range including every value between the minimum and maximum values recited as well as any ranges that can be formable thereby.

The instant invention pertains to methods of treating a multiple myeloma and Waldenström's macroglobulinemia by inhibiting interaction of BlyS and/or APRIL with their receptors. Specifically, the methods utilize an inhibitor which is a fusion molecule comprising TACI extracellular domain or a fragment thereof and binds BlyS and/or APRIL and 2) a human immunoglobulin-constant domain. The methods of the invention utilize a fusion molecule comprising a human immunoglobulin-constant domain and any polypeptide with at least 50% identity, and preferably 60%, 65%, 70%, 75%, 80%, 85%, 90%, 95% or 99% identity to TACI extracellular domain that can bind BlyS and/or APRIL ligands. U.S. Pat. Nos. 5,969,102, 6,316,222 and 6,500,428 and U.S. patent application Ser. Nos. 09/569,245 and 09/627,206 (teachings of which are incorporated herein in their entirety by reference) disclose sequences for the extracellular domain of TACI as well as specific fragments of the TACI extracellular domain that interact with TACI ligands, including BlyS and APRIL. One preferred fragment of the extracellular domain of TACI comprises one or two cysteine repeat motifs. Another preferred fragment is a fragment comprising amino acids 30-110 of the extracellular domain of TACI. Another preferred fragment is a fragment comprising amino acids 1-154 of the extracellular domain of TACI (SEQ ID NO: 1). Any of the fusion molecules used in the methods of the instant invention can be referred to as a TACI-Ig fusion molecule.

TACI-Fc5 is one of the TACI-Ig fusion molecules useful for the methods of the instant invention. TACI-Fc5 is a fusion polypeptide molecule comprising from about amino acid 1 to about amino acid 154 (SEQ ID NO: 1) of TACI extracellular domain and a modified Fc portion of human IgG (SEQ ID NO: 2). Other TACI-Ig molecules useful for the methods of the instant invention include a fusion molecule comprising polypeptide with SEQ ID NO: 2 and a polypeptide which can bind BlyS and which is at least 50%, preferably 60%, 65%, 70%, 75%, 80%, 85%, 90%, 95% or 99% amino acid sequence identical to the sequence set out as SEQ ID NO: 1.

Preferred embodiments of the invention include methods of using a TACI-Ig fusion molecule for treating multiple myeloma (MM) and Waldenström's macroglobulinemia (WM), other hematological malignancies, autoimmune diseases such as rheumatoid arthritis and systemic lupus erythematosus or to decrease the number of circulating mature B-cells and immunoglobulin-secreting cells and soluble immunoglobulins associated with such diseases.

When treating MM and WM patients with a TACI-Ig fusion molecule, a protocol depicted in FIG. 1 may be used. Patients are given injections of a TACI-Ig fusion molecule at concentrations in a range from 2 to 10 mg/kg. Further details of this protocol are set out in Example 3. After receiving five injections, the patients are monitored during the following four weeks for signs of improvement or stabilization of their disease. Patients are classified into five different groups depending on their response to treatment with a TACI-Ig fusion molecule: Complete Response (CR), Very Good Partial Response (VGPR), Partial response (PR), stable disease (SD), progressive disease (PD). Criteria for each of the five groups are listed in Table 4 below.

TABLE 4

RESPONSE CRITERIA

| | M-protein | Bone marrow plasmacytosis | Other |
|---|---|---|---|
| For MM patients | | | |
| Complete response (CR) | absence of M protein in serum and urine as assessed by a negative immunofixation | <5% plasma cells in the bone marrow aspirate | No signs of worsening anemia<br>No increase in serum calcium levels<br>No new lytic bone lesions |
| Very Good Partial response (VGPR) | greater than or equal to 90% reduction in serum M protein as assessed by electrophoresis and/or greater than or equal to 90% (200 mg/24 h) reduction in urine M protein as assessed by electrophoresis | | No signs of worsening anemia<br>No increase in serum calcium levels<br>No new lytic bone lesions |
| Partial response (PR) | greater than or equal to 50% reduction in serum M protein as assessed by electrophoresis and/or greater than or equal to 90% (200 mg/24 h) reduction in urine M protein as assessed by electrophoresis | | No signs of worsening anemia No increase in serum calcium levels No new lytic bone lesions |
| Stable disease (SD) | not meeting criteria for response or progressive disease | | |
| Progressive disease (PD) | greater than 25% increase in M protein | >25% increase in plasma cells in the bone marrow aspirate | Increase in size of existing bone lesions<br>Development of new bone lesions or soft tissue plasmacytoma<br>Development of hypercalcemia |
| For WM patients | | | |
| Complete response (CR) | absence of M protein in serum and urine as assessed by a negative immunofixation | <5% Lymphoplasmocytes in the bone marrow aspirate | Disappearance of symptoms (anemia, cryoglobulinemia) and tumoral mass, including lymph nodes, enlarged spleen and liver (Cheson 1999) |
| Partial response (PR) | greater than or equal to 50% reduction in serum M protein as assessed by electrophoresis and/or greater than or equal to 90% reduction in urine M protein as assessed by electrophoresis | | greater or equal than 50% reduction in SPO (sum product of greatest parameters) in tumor mass, including lymph node, enlarged spleen and liver Improvement in clinical manifestations (anemia, cryoglobulinemia or peripheral neuropathy) |
| Stable disease (SD) | not meeting criteria for response or progressive disease | | |
| Progressive disease (PD) | greater than 25% increase in M protein | >25% increase in lymphoplasmocytes in the bone marrow aspirate | Increase in size of the tumor mass including lymph node, enlarged spleen and liver |

The patient's condition is classified as "relapse from complete response" if any of the following occurs: reappearance of serum or urinary paraprotein on immunofixation or routine electrophoresis confirmed by at least one further investigation and excluding oligoclonal immune reconstitution; >5% plasma cells in a bone marrow aspirate or on a trephine bone biopsy; development of new lytic lesions or soft tissue plasmacytomas or definite increase in the size of residual bone lesions; or development of hypercalcemia (corrected serum calcium>11.5 mg/dl or 2.8 mmol/l) not attributable to any other cause.

The patient's condition is classified as "progressive disease" (for patients not in complete response), if one or more of the following occurs: ≥25% increase in the level of the serum monoclonal paraprotein, which must also be an absolute increase of at least 5 g/l and confirmed by at least one repeated investigation; ≥25% increase in the 24 hour urinary light chain excretion, which must also be an absolute increase of at least 200 mg in 24 hours and confirmed by at least one repeated investigation; ≥25% increase in plasma cells in a bone marrow aspirate or on trephine biopsy, which must also be an absolute increase of at least 10%; definite increase in the size of existing bone lesions or soft tissue plasmacytomas (development of a compression fracture does not exclude continued response and may not indicate progression); development of new bone lesions or soft tissue plasmacytomas (development of a compression fracture does not exclude continued response and may not indicate progression); development of hypercalcemia (corrected serum calcium>11.5 mg/dl or 2.8 mmol/l) not attributable to any other cause.

The patient's condition can be classified as improving if after first five injections, any of the following is detected: decrease of immunoglobulin IgA, IgG, IgM or IgD free light chain in patient's blood sample; decrease of immunoglobulin IgA, IgG, IgM or IgD free light chain in patient's blood sample; decrease of M-protein as determined by immunofixation in patient's blood sample; decrease of M-protein as determined by electrophoresis in patient's blood sample; decrease of LDH, soluble syndecan-1 or beta-2 microglobulin in patient's blood sample; decrease in patient's lymphocyte cell count as determined by flow cytometry; decrease of Bence-Jones protein as detected by immunofixation or electrophoresis in patient's urine sample; decrease of percentage of plasma cells or lymphocyte cells, PCLI, Ki-67 or BlyS/APRIL receptors in patient's bone marrow sample.

Table 5 provides an exemplary schedule for assessing the efficiency of treatment with a TACI-Ig fusion molecule.

TABLE 5

Schedule of Treatment Assessments

| | Treatment period cycle 1 | | | | | Post-Treatment Follow-Up cycle 1 | | |
|---|---|---|---|---|---|---|---|---|
| | Day 1 First day of treatment | Day 8 end of week-1 | Day 15 end of week-2 | Day 22 end of week-3 | Day 29 end of treatment visit cycle 1 | Day 36 end of week-5 | Day 43 end of week-6 | Day 50 end of week-7 |
| Informed consent to enter Extension study | | | | | | | | |
| TACI-Ig doses[1] | x | x | x | x | x | | | |
| Physical examination (including weight and vital signs) | x | x | x | x | x | x | x | x |
| ECOG | | | | | | | | |
| ECG | | | | | | | | |
| Ejection fraction measurement (by echocardiography or scintigraphy) | | | | | | | | |
| Skeletal survey (X-ray) | | | | | | | | |
| MRI | | | | | | | | |
| CT scan and/or ultrasound scan (only for WM patients) | | | | | | | | |
| Blood sampling for | | | | | | | | |
| Hematology | x | x | x | x | x | x | x | x |
| Coagulation | | | | | | | | |
| Blood chemistry[2] | x | x | x | x | x | x | x | x |
| IgA/IgG/IgM quantification (IgD for IgD myeloma) | | x | x | x | x | x | x | x |
| Serum free light chain | | x | x | x | x | x | x | x |
| M-protein detection by immunofixation | | | | | x | | | |
| M-protein quantification by electrophoresis | | x | x | x | x | x | x | x |
| CRP/LDH | | x | x | x | x | x | x | x |
| Soluble syndecan-1 | | x | x | x | x | x | x | x |
| Beta2-microglobulin | | x | x | x | x | x | x | x |
| Lymphocyte cell count by flow cytometry | | x | x | x | x | x | x | x |
| Urine sampling for | | | | | | | | |
| Urinalysis (dipstick analysis) | x | x | x | x | x | x | x | x |
| Proteinuria (24-h urine) | | x | x | x | x | x | x | x |

TABLE 5-continued

Schedule of Treatment Assessments

| | Treatment period cycle 1 | | | | Post-Treatment Follow-Up cycle 1 | | |
|---|---|---|---|---|---|---|---|
| | Day 1 First day of treatment | Day 8 end of week-1 | Day 15 end of week-2 | Day 22 end of week-3 | Day 29 end of treatment visit cycle 1 | Day 36 end of week-5 | Day 43 end of week-6 | Day 50 end of week-7 |
| Bence-Jones protein detection by immunofixation | | | | | x | | | |
| Bence-Jones protein quantification by electrophoresis | | x | x | x | x | x | x | x |
| Bone marrow aspirate for | | | | | | | | |
| % plasma cell determination | | | | | | | | |
| PCLI/KI67[3] | | | | | | | | |
| BLyS and APRIL receptors by RT-PCR and flow cytometry | | | | | | | | |
| Lymphocyte cell count by flow cytometry | | | | | | | | |
| Adverse Event Monitoring | | | | | | | | |
| Concomitant Medication/Procedures Recording | | | | | | | | |

Patients whose condition is classified at least as stabilized after the first cycle of treatment with a TACI-Ig fusion molecule, may receive at least two additional cycles of treatment with the fusion molecule. FIGS. 4 and 5 provide one example of a protocol for such additional cycles of treatment. On day 1 of each of the subsequent cycles, patients are given injections of a TACI-Ig fusion molecule at concentrations in a range from 2 to 10 mg/kg. After receiving five injections, the patients are monitored during the following four weeks for signs of improvement or stabilization of their condition. It can be concluded that such improvements have occurred, if any of the following is detected: decrease of immunoglobulin IgA, IgG, IgM or IgD free light chain in patient's blood sample; decrease of M-protein as determined by immunofixation in patient's blood sample; decrease of M-protein as determined by electrophoresis in patient's blood sample; decrease of LDH, soluble syndecan-1 or Beta-2 microglobulin in patient's blood sample; decrease in patient's lymphocyte cell count as determined by flow cytometry; decrease of Bence-Jones protein as detected by immunofixation or electrophoresis in patient's urine sample; decrease of percentage of plasma cells or lymphocyte cells, PCLI, Ki-67 or BlyS/APRIL receptors in patient's bone marrow sample.

To select an optimal dose for treating a specific patient's condition, a dose-escalation decision tree (FIG. 3) was developed. According to the design tree (FIG. 3), if 0 subjects out of 3 in a given cohort experiences dose limiting toxicity (DLT), escalation may be advanced to the next sequential cohort. If 1 subject out of 3 in a given cohort experience DLT, an additional 3 subjects will be enrolled in that dose cohort. If 1 subject out of 6 experiences DLT, escalation may be advanced to the next dose. If >1 subject out of 6 experience DLT, dose de-escalation occurs and 3 subjects will be treated at an intermediate dose that elicited DLT and the next lower dose. If 0 subjects out of 3 experiences DLT at the intermediate dose, then enrollment is halted and the intermediate dose is declared the MTD (Maximum Tolerated Dose). If 1 subject out of 3 experiences DLT at the intermediate dose, then enrollment is halted and the dose level below is declared the MTD. If >1 subject out of 3 in a given cohort experience DLT, dose de-escalation occurs and 3 subjects will be treated at an intermediate dose to be specified by the Safety Monitoring Committee between the dose that elicited DLT and the next lower dose. If 0 subject out of 3 experiences DLT at the intermediate dose, then enrollment is halted and the intermediate dose is declared the MTD. If 1 subject out of 3 experiences DLT at the intermediate dose, then enrollment is halted and the dose level below is declared MTD. De-escalation will also be applicable in case DLTs are observed at the starting dose.

Figure 6:
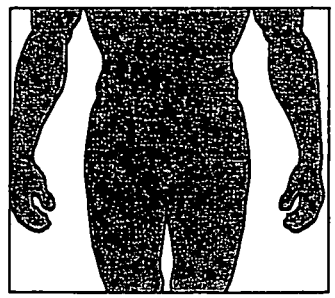
FIG. 6. Administration of TACI-Ig. Possible zones for subcutaneous injections. 1—right upper external area, 2—left lower external area, 3—right lower external area, 4—left upper external area, 5—median lower area.

A fusion TACI-Ig molecule can be delivered via subcutaneous injections into the anterior abdominal wall using a syringe, preferably a 1.5 ml syringe with 25 G needles. When more than one injection is required to administer a dose, the injections are administered a few centimeters apart and as close as possible in time. For repeated drug administration it is advisable to rotate the site of administration on the anterior abdominal wall. The possible zones for subcutaneous injection into the anterior abdominal wall are depicted in FIG. 6 and include right upper external area, left lower external area, right lower external area, left upper external area and median lower area. Alternatively, a TACI-Ig fusion molecule of the invention can be delivered via intravenous injections or orally in a form of tablets, caplets, liquid compositions or gels.

Methods of the invention can be combined with other methods of MM and WM treatment such as chemotherapy, radiation or surgery. A patient can be treated by methods of the invention prior or simultaneously and more preferable after the patient is subjected to chemotherapy, radiation and/or surgery. A fusion molecule of the invention can be administered concomitantly with other medications beneficial for a patient. Such medications may include, but are not limited, to bisphosphonates, erythropoietin, granulocyte growth factors or granulocyte colony stimulating factor or drugs for the management of pain, melphalan, vincristine, doxorubicin, thalidomide, nucleoside analogs and proteosome inhibitors, including but not limited to bortezomib.

TACI-Ig may be given alone or in combination with bortezomib. TACI-Ig may be dosed as above and bortezomib may be given at a dose of 1.3 mg/m² twice weekly for two weeks, followed by a rest period of ten days. This is one cycle of treament. Preferably bortezomib is given intravenously. The response to treatment is monitored as described above for TACI-Ig alone, and additional treatment cycles of TACI-Ig and or bortezomib may be administered. TACI-Ig may be administered at a dose as described above or at a lower dose in combination with bortezomib at a dose as described or at a lower dose of bortezomib. Doses of TACI-Ig and bortezomib may be given concurrently or in alternating doses of TACI-Ig followed by a cycle of bortezomib or a cycle of bortezomib followed by a cycle of TACI-Ig. This dosing may be repeated.

TACI-Ig may be administered to those multiple myeloma patients who have become resistant to or who do not respond to other methods of treatment, including but not limited to treatment with bortezomib.

All U.S. Patents and published patent applications listed herein are hereby incorporated by reference in their entirety.

EXAMPLES

The following examples illustrate various embodiments of the present invention are not to be construed as limiting the invention in any way.

Example 1

Testing TACI-Fc5 Pharmacology, Toxicology and Pharmacokinetics in an Experimental Animal Model To test effect of TACI-Fc5 on respiratory parameters, the no-observed effect level (NOEL) of TACI-Fc5 on respiratory parameters in conscious mice was studied and was found to be at least 80 mg/kg when administered by the subcutaneous route.

Behavioral Irwin Test and Effect on Body Temperature were performed by administering single doses of 5, 20 and 80 mg/kg of TACI-Fc5 by the subcutaneous route to groups of 8 male mice. The NOEL of these injections was 20 mg/kg by the subcutaneous route for behavioral Irwin test and effect on body temperature. Minor and transient stimulant effects were seen at the highest dose of 80 mg/kg.

To determine the effect of TACI-Fc5 on blood pressure and heart rate, TACI-Fc5 was administered to conscious cynomoglus monkeys by the subcutaneous route at doses of 20 and 80 mg/kg. The injections did not induce any change in arterial blood pressure, heart rate or electrocardiogram. The NOEL for cardiovascular parameters when administered by the subcutanous route in conscious cynomolgus monkeys corresponds to at least 80 mg/kg.

When administered to mice as a single dose by the intravenous (IV) or subcutaneous (SC) route, TACI-Fc5 did not induce mortality or appreciable general or local abnormal effects in the animals up to the highest technically feasible dose: 1200 mg/kg. Furthermore, the administration of TACI-Fc5 to monkeys as a single dose by the SC route at the dose level of 240 mg/kg did not result in mortality nor did it result in any major toxic effects.

On the basis of the results obtained after two (2) or four (4) weeks of administration of TACI-Fc5 by subcutaneous route to mice at the doses of 5, 20 and 80 mg/kg/every second day followed by four (4) weeks of recovery it was concluded that the compound is well tolerated in this species at doses up to 80 mg/kg. Treatment-related modifications confined to the immune system were revealed at all doses. These changes involved decreases in total and mature B cell numbers and IgG and IgM serum levels. Immunohistochemistry tests done in the spleen and lymph nodes confirmed depletion confined to B cells, with T cell number remaining unchanged. All these alterations, time- and dose-related in some cases, were considered as exaggerated pharmacological effects as expected in a responsive species after administration of very high doses of TACI-Fc5.

Overall, these effects were seen after two (2) and four (4) weeks of treatment, without major indications of progression with time. They appeared to be almost completely reversible after four (4) weeks of withdrawal of treatment, except for decreased B cell counts.

In order to ascertain B-cell modulation reversibility, a further study in mice was conducted at the doses of 5 and 20 mg/kg given every second day for four (4) weeks, with longer recovery periods. Recovery of total and mature circulating B cells was reached after two (2) months of withdrawal at 5 mg/kg, and after four (4) months at 20 mg/kg. Moreover, the injection induced a slight increase, compared to vehicle controls, of inflammatory changes at the injection sites at all doses.

Subcutaneous administration of TACI-Fc5 in monkeys did not induce major signs of toxicity at any of the doses tested, 5, 20 or 80 mg/kg/every third day, when given for four (4) consecutive weeks followed by four (4) weeks of recovery.

Local tolerability was satisfactory up to and including the highest dose tested. Dose-related and reversible slight or moderate changes of inflammatory origin (mainly perivascular mononuclear and eosinophilic cell infiltrates) were induced, but were mainly related to the local presence of exogenous proteins. Only at the high dose, a few animals showed slight or moderate subacute inflammation associated with a cyst formation.

Circulating B-cell number decreases at the lymphocyte subset determinations, as well as histological depletion of the spleen follicular marginal zone (known to be a B-cell dependent area) and decreases in total IgG and IgM serum levels were seen. They were the result of the pharmacodynamic properties of TACI-Fc5, as shown by in vitro and in vivo pharmacology experiments. Their degree was exaggerated, as expected in toxicology studies in which animals are purposely administered high doses of the test compound. While low serum IgG and IgM levels and spleen lymphocytic depletion showed a clear tendency towards recovery within the one-month withdrawal period allowed, total and mature circulating B cells did not show a similar behavior, indicating a longer time needed to recover.

At the end of the treatment period (week 4), males and females of the high dose group (80 mg/kg) showed a slight but statistically significant decrease in mean total protein values compared to controls. A slight trend towards decrease was also seen at the same dose in week 2, and at the end of the recovery period.

Serum protein modifications in the high dose females at the end of the dosing period included a decrease in globulin and increases in albumin percentage and alpha 1 globulin fraction. Alpha 1 globulin fraction also appeared higher than controls in group 3 females (20 mg/kg).

Immunogenicity of TACI-Fc5 was low in both mice. There was no evidence of neutralizing antibodies in either species.

Histological examination of the reproductive organs of mice from the two (2)- and four (4)-week SC toxicity study did not show a signal of treatment-related effects.

The local tolerance study showed that TACI-Fc5 was well tolerated locally when injected by the subcutaneous route to rabbits, at the dose of 70 mg/mL.

A single dose pharmacokinetic study was conducted in mice by either the intravenous route, at the dose of 1 mg/kg, or the subcutaneous route, at the doses of 1, 5 and 15 mg/kg.

Time to maximal absorption ($t_{max}$) was estimated between four (4) h to 16 h, with a $T_{1/2}$ calculated to be around 40-50 h.

An infusion-like profile was observed during the first 30 minutes after IV bolus administration, after which TACI-Fc5 was eliminated from the body with an elimination half-life of 44 h. After subcutaneous administration, the ratio between the Area Under the Curves obtained at the three (3) doses of 1, 5 and 15 mg/kg was 1:5:8 vs. the dose ratio of 1:5:15, suggesting a loss of dose-proportionality at the high dose.

TACI-Fc5's bioavailability by the subcutaneous route was 76% and 89% at the doses of 1 and 5 mg/kg respectively, but was lower than expected at 15 mg/kg (0.42; calculated vs. the intravenous 1 mg/kg dose) in mice. Since the apparent elimination half-life was not altered, the lower bioavailability observed at the high dose could be explained by an increase of both clearance and volume of distribution or more probably by a decreased absorption due to the formation of a deposit at the site of injection.

A single dose pharmacokinetic study was conducted in six male cynomolgus monkeys injected by either the intravenous route, at the dose of 1 mg/kg, or the subcutaneous route, at the doses of 1, 5 and 15 mg/kg.

Six male monkeys were divided into two (2) groups of three (3) animals each and received two (2) administrations separated by a wash-out period of 2 weeks. Treatments of period one (1) were 1 mg/kg IV (group 1) and 1 mg/kg SC (group 2) and treatments of period two (2) were 5 mg/kg SC (group 1) and 15 mg/kg SC (group 2). Time to maximal absorption ($t_{max}$) was estimated between 6 h to 8 h, with a $t_{1/2}$ calculated to be around 120-190 h.

An infusion-like profile was observed in two out of three monkeys during the first 15 min after IV bolus administration, after which TACI-Fc5 was eliminated from the body with an elimination half-life of 179±29 h. The volume of distribution at the steady state, $V_{ss}$, was 382±82 mL/kg, a volume near the intracellular fluid volume.

After subcutaneous administration, the Area Under the Curve (AUC) vs. dose proportionality was good, i.e. 216, 1182 and 2732 h μg/mL for SC doses of 1, 5 and 15 mg/kg. The TACI-Fc5 bioavailability by the subcutaneous route (calculated vs. the 1 mg/kg IV dose) was 0.92, 1.02 and 0.77 at the low, intermediate and high doses. This demonstrates that, TACI-Fc5 was almost completely absorbed by the subcutaneous route.

Low levels of TACI-Fc5 were found in the pre-dose samples for period 2 (between doses of 1 mg/kg by IV or SC routes, period 1, and doses of 5 or 15 mg/kg, respectively, in period 2) for all six monkeys, since during the two (2)-week washout period only two (2) half-lives had elapsed, which was insufficient for a complete elimination of the administered compound five ((5) half-lives required). However, the Area Under the Curve contribution of the previous dose could be estimated to represent only about 2% of the total Area Under the Curve in period 2.

IgG serun levels showed a 10.2% decrease after IV dosing. The 15 mg/kg SC dose showed a slightly higher effect, while no differences were observed between the 1 and the 5 mg/kg SC doses (decreases of 8.6%, 8.4% and 12.3% after 1, 5 and 15 mg/kg doses respectively). IgM serum levels showed an 18.0% decrease after IV dosing. No differences were observed between the 3 SC doses (decreases of 23.5%, 23.0% and 24.2% after 1, 5 and 15 mg/kg doses respectively).

Example 2

Determining TACI-Fc5 Tolerable Dose in Healthy Volunteers

A single ascending dose study was performed in healthy volunteers. Specifically, TACI-Fc5 was tested in humans in a double blind, single ascending dose study in healthy male volunteers. In this study, TACI-Fc5 was shown to be safe and well tolerated at doses of 2.1 mg, 70 mg, 210 mg and 630 mg (equivalent to doses of around 0.03, 1, 3 and 9 mg/kg). The particulars of the study are summarized in Table 1 below.

TABLE 1

| Study Description | | | | |
|---|---|---|---|---|
| Design | N° Volunteers | Dose TACI-Fc5 | Route(s) administration | Assessments |
| Randomized, double-blind, placebo-controlled | 23 healthy males | Escalating doses ranging from 2.1 mg to 630 mg | sc | Safety, tolerability, pharmacokinetics and pharmacodynamics |

Four groups of subjects were recruited. In each dosing group, one subject was randomized to receive a placebo injection, with all others receiving TACI-Fc5. Following discharge from the investigational site at 24 hours post dose, subjects attended scheduled assessments on an outpatient basis for seven weeks. Systemic and local tolerability of TACI-Fc5 were monitored by physical examination findings, injection site pain, local tolerability reactions at the site of injection(s) (redness, swelling, bruising and itching), vital signs, 12-lead ECGs, safety laboratory assessments and recording of adverse events.

Pharmacokinetic and pharmacodynamic markers were monitored throughout the seven-week period following dosing. The pharmacodynamic effect of TACI-Fc5 was monitored using a number of markers including: lymphocyte subsets by FACS analysis: plasma cells (CD138+), immature B-cells (CD19+, IgD−), mature B-cells (CD19+, IgD+), T-helper cells (CD5+, CD4+), cytotoxic T-cells (CD5+, CD8+), total T-cells (CD5+), free BLyS, BLyS/TACI-Fc5 complex, IgG, IgM, anti-TACI-Fc5 antibodies.

Dose escalation was guided by an algorithm (except for group 1) within the study protocol, based upon a review of data three weeks after dosing. Four groups were dosed: group 1 received 2.1 mg (equivalent to around 0.03 mg/kg); group 2 received 70 mg (equivalent to around 1 mg/kg), group 3 received 210 mg (equivalent to around 3 mg/kg), group 4 received 630 mg (equivalent to around 9 mg/kg).

The study showed that TACI-Fc5 was well tolerated in all groups. There were no apparent effects upon physical examination findings, vital signs or 12-lead ECGs.

Transient redness and swelling was observed at the site of administration in some subjects, with redness affecting all subjects in cohorts 3 and 4. Although the incidence of injection site reactions appears to be increased in higher dose groups it is believed that this is related to the increased volume (and number) of injections.

Forty-eight (48) treatment emergent adverse events were reported in the seven weeks following dosing. The majority of these (44 events, 91.7%) were mild, with the remainder being moderate (4 events, 8.3%). There were no severe adverse events and no serious adverse events during this period. There was no apparent relationship between the doses of TACI-Fc5 administered and the incidence, intensity or assigned relationship of adverse events. The adverse events reported to date are summarized in Table 2.

formed using nominal sampling times, after subtraction of pre-dose concentrations that were present in subjects 2, 6 and 13. Pharmacokinetic parameters following single subcutaneous doses between 2.1 mg and 630 mg in study are summarized in Table 3. Drug concentrations were close to the limit of quantification of the assay following the 2.1 mg dose of TACI-Fc5, limiting the value of the data at this dose level. At doses of 70 mg and above, $T_{max}$ (time to maximal absorption) ranged from 16 to 36 hours and the overall median $t_{1/2}$ (cal-

TABLE 2

List of Treatment-Emergent Adverse Events

| | | Treatment | | | | | | |
|---|---|---|---|---|---|---|---|---|
| Body System | Preferred Term | TACI-Fc5 2.1 mg N | TACI-Fc5 70 mg N | TACI-Fc5 210 mg N | TACI-Fc5 630 mg N | Placebo N | Total N | % |
| Eye Disorders | Eyelid Oedema | 1 | | | | | 1 | 2.1 |
| Gastrointestinal disorders | Abdominal pain upper | | | | 1 | | 1 | 2.1 |
| | Diarrhea | | 1 | 1 | 1 | 1 | 4 | 8.5 |
| | Mouth ulceration | | | | 1 | 1 | 2 | 4.3 |
| | Nausea | | 1 | | 1 | 1 | 3 | 6.4 |
| | Vomiting | | | 1 | 1 | | 2 | 4.3 |
| General disorders and administration site conditions | Influenza-like illness | | | | 1 | 2 | 3 | 6.4 |
| Infections and infestations | Nasopharyngitis | | 4 | 1 | 1 | | 6 | 10.6 |
| | Perianal abscess | 1 | | | | | 1 | 2.1 |
| Injury, poisoning and procedural complications | Contusion | | | | 1 | | 1 | 2.1 |
| | Joint Injury | | | 1 | | | 1 | 2.1 |
| Musculoskeletal and connective tissue disorders | Arthralgia | | 1 | | | | 1 | 2.1 |
| | Back Pain | | | | 1 | | 1 | 2.1 |
| Nervous system disorders | Headache | 1 | 2 | 2 | 2 | 1 | 8 | 17.0 |
| Respiratory, thoracic and mediastinal disorders | Cough | | 1 | | 1 | 1 | 3 | 6.4 |
| | Nasal congestion | | | 1 | | 1 | 2 | 4.3 |
| | Pharyngolaryngeal pain | 1 | 2 | 1 | 2 | 1 | 7 | 14.9 |
| Skin and subcutaneous tissue disorders | Rash generalized | | | | 1 | | 1 | 2.1 |

In summary, TACI-Fc5 was well tolerated at doses up to 630 mg with no significant safety concerns being raised.

A non-compartmental analysis of TACI-Fc5 concentrations was also performed. This preliminary analysis was perculated from the terminal portion of the curve) was 303 hours. In addition, the Area Under the Curve (extrapolated to infinity) and the $C_{max}$ increased in a greater than dose proportional manner.

TABLE 3

PK parameters

| Parameter | Treatment | n | Mean | sd | Min | Median | Max | CV |
|---|---|---|---|---|---|---|---|---|
| $C_{max}$ (Jlg/mL) | 2.1 mg | 5 | 0.015 | 0.011 | 0.005 | 0.013 | 0.032 | 74 |
| $T_{max}$ (h) | 2.1 mg | 5 | | | 8 | n | 336 | |
| $t_{1/2}$ (h) | 2.1 mg | 4 | 204 | 180 | 45 | 203 | 365 | 88 |
| AUC (h · ug/mL) | 2.1 mg | 4 | 8.55 | 9.65 | 0.524 | 6.62 | 20.4 | 113 |
| % AUCextrap | 2.1 mg | 4 | 36 | 24 | 13 | 32 | 69 | 65 |
| CL/F (L/h) | 2.1 mg | 4 | 1.70 | 1.90 | 0.10 | 1.34 | 4.01 | 112 |
| $C_{max}$ (ug/mL) | 70 mg | 5 | 0.617 | 0.236 | 0.426 | 0.496 | 0.985 | 38 |
| $T_{max}$ (h) | 70 mg | 5 | | | 16 | 16 | 36 | |

TABLE 3-continued

PK parameters

| Parameter | Treatment | n | Mean | sd | Min | Median | Max | CV |
|---|---|---|---|---|---|---|---|---|
| $t_{1/2}$ (h) | 70 mg | 5 | 255 | 23 | 219 | 264 | 276 | 9 |
| AUC (h · ug/mL) | 70 mg | 5 | 79.7 | 15.7 | 65.4 | n.5 | 101 | 20 |
| % AUCextrap | 70 mg | 5 | 10 | 1 | 9 | 11 | 11 | 12 |
| CL/F (L/h) | 70 mg | 5 | 0.90 | 0.17 | 0.69 | 0.97 | 1.07 | 18 |
| $C_{max}$ (ug/mL) | 210 mg | 5 | 3.00 | 0.902 | 1.84 | 2.90 | 4.16 | 30 |
| $T_{max}$ (h) | 210 mg | 5 | | | 12 | 16 | 36 | |
| $t_{1/2}$ (h) | 210 mg | 5 | 429 | 160 | 169 | 433 | 568 | 37 |
| AUC (h · ug/mL) | 210 mg | 5 | 260 | n | 167 | 267 | 344 | 28 |
| % AUCextrap | 210 mg | 5 | 6 | 3 | 1 | 6 | 9 | 54 |
| CL/F (L/h) | 210 mg | 5 | 0.86 | 0.26 | 0.61 | 0.79 | 1.25 | 31 |
| $C_{max}$ (ug/mL) | 630 mg | 4 | 13.9 | 2.79 | 11.4 | 13.7 | 16.7 | 20 |
| $T_{max}$ (h) | 630 mg | 4 | | | 16 | 16 | 16 | |
| $t^{1/2}$ (h) | 630 mg | 4 | 313 | 16 | 291 | 316 | 329 | 5 |
| AUC (h · ug/mL) | 630 mg | 4 | 992 | 194 | 719 | 1040 | 1170 | 20 |
| % AUCextrap | 630 mg | 4 | 2 | 0 | 1 | 2 | 2 | 18 |
| CL/F (L/h) | 630 mg | 4 | 0.66 | 0.15 | 0.54 | 0.61 | 0.88 | 23 |

Pharmacodynamic analyses have shown reductions in baseline IgM levels in the seven weeks following single doses of 70, 210 or 630 mg. Although no clear dose response relationship could be established with the small sample size in the study, the extent of the IgM reduction was greatest in the highest dose group. Subjects in the 70 mg dose group appeared to show a return of IgM levels towards baseline by seven weeks post dose. Levels in the higher dose groups remained suppressed at this time point. There were no apparent effects upon IgG levels, or upon the lymphocyte subpopulations that were measured by FACS.

Levels of BLyS/TACI-Fc5 complexes were shown to increase proportionately during the sampling period, reaching a plateau by approximately 600 hours post dose.

Following a single subcutaneous injection of 70 to 630 mg (equivalent to doses of around 1 to 9 mg/kg) of TACI-Fc5 to healthy male subjects, the $T_{max}$ (time to maximal absorption) ranged from 16 to 36 hours and the overall median $t_{1/2}$ (calculated from the terminal portion of the curve) was 303 hours. In addition, the Area Under the Curve (extrapolated to infinity) and the $C_{max}$ increased in a greater than dose proportional manner. A pharmacodynamic effect was noted upon IgM levels at doses of 70, 210 and 630 mg. There was no apparent effect of treatment upon IgG or lymphocyte subpopulations following a single dose of TACI-Fc5.

Example 3

Treating Multiple Myeloma (MM) and Waldenström's Macroglobulinemia (WM) Patients with TACI-Fc5 Compositions MM and WM patients received five consecutive weekly administrations of TACI-Fc5 on protocol depicted in FIG. 1. The treatment followed a sequential dose-escalation cohort design outlined in FIG. 2. Three patients were enrolled at the first dose level (2 mg/kg). Once the last patient received his/her five injections, the dose was escalated.

Dose levels initially administered were 2, 4, 7 or 10 mg/kg (FIG. 2). TACI-Fc5 was administered by subcutaneous injection on days 1, 8, 15, 22 and 29 of a 57-day cycle. A total of 16 patients entered the trial, 11 MM patients and 4 WM patients were treated. No dose limiting toxicity was observed and no serious adverse event related to TACI-Fc5 was reported. Five MM patients and 3 WM patients had stable disease after the first treatment cycle; the rest of the patients progressed. Eight patients entered the extension phase: 4 received two additional cycles and 4 received 15 weekly injections. Seven of the eight patients completed the extension phase: four patients with stabke disease (three MM and one WM), two patients with progressive disease and one WM patient with a minimal response (M-component descrese superior to 25%). Polyclonal immunoglobulins in all MM patients and soluble syndecan-1 in 2/5 MM patients showed a marked decrease during treatment, while the C-reactive protein was not affected by the treatment. Lymphocyte subset analysis showed that plasmocytes were selectively decreased while T lymphocytes were unchanged.

Treatment with TACI-Fc5 was well tolerated at the dose levels administered to the patients. A marked biological response was observed in accordance with the expected TACI-Fc5 mode of action.

Example 4

Evaluating Patient's Response for TACI-Fc5 Treatment

Before administration of the first dose of TACI-Fc5 medication, the following assessments were performed: complaint-directed physical examination, including body weight and vital signs ECOG performance status, routine laboratory tests such as hematology, blood chemistry urinalysis, blood sampling for determination of PK/PD parameters, recording of concomitant medication and recording of adverse events.

Post-dose day 1, patients were hospitalized in the clinical research unit for the first 24 h following the first dose of TACI-Fc5. During this period the following assessments were performed: complaint-directed physical examination, including vital signs: 1 h, 2 h, 4 h, 8 h, 16 h and 24 h post-dose; blood sampling for determination of PK parameters at 2 h, 4 h, between 6-12 h and 24 h post-dose, recording of concomitant medication and recording of adverse events.

On day 3 or 4 the following procedures were performed: complaint-directed physical examination, including vital signs: 48 h or 72 h post-dose; blood sampling for determination of PK parameters: 48 h or 72 h post the first dose of TACI-Fc5.

Pre-dose on days 8, 15, 22 and 29, the following procedures were performed: complaint-directed physical examination, including body weight and vital signs; routine laboratory tests such as hematology, blood chemistry, urinalysis, specific disease assessment laboratory tests, blood sampling for immunoglobulin quantification, serum free light chain, M-protein detection by immunofixation, M-protein quantification by electrophoresis, C-reactive protein, LDH, soluble syndecan-1, Beta-2 microglobulin, lymphocyte cell count by flow cytometry, urine sampling for: proteinuria (24 h-urine), Bence-Jones protein detection by immunofixation, Bence-Jones protein quantification by electrophoresis, bone marrow aspiration for: % plasma cell determination, PCLI, Ki67; lymphocyte cell count by flow cytometry; blood sampling for determination of PK/PD parameters; recording of concomitant medication and recording of adverse events.

At days 8, 15, 22 and 29, patients were administered additional injections of TACI-Fc5 at the same concentrations as those administered on the first date of treatment.

At day 30 of the treatment cycle, PK parameters for each of the patients were determined by analyzing a blood sample of each of the patients.

At days 36, 43, 50 and 57, complain-directed examinations were performed, including body weight and vital signs. At day 57, 12-lead ECG, skeletal survey (X-ray) and MRI were performed. In WM patients at day 57, measurement of tumor lesions by CT scan and/or ultrasound scan of the thoracic/abdominal/pelvic region were also performed.

All patients were subjected to routine and disease specific laboratory tests such as immunoglobulin quantification, serum free light chain quantification, M-protein detection by immunofixation, M-protein quantification by electrophoresis, C-reactive protein, LDH, soluble syndecan-1, Beta-2 microglobulin, lymphocyte cell count by flow cytometry, urine sampling for proteinuria (24 h-urine), Bence-Jones protein detection by immunofixation, Bence-Jones protein quantification by electrophoresis, bone marrow aspiration for % plasma cell determination, PCLI, Ki67, lymphocyte cell count by flow cytometry, BlyS and APRIL receptors by RT-PCR and flow cytometry.

Various MM and WM disease associated markers were measured in the patients at day 57. Treatment with TACI-FC5 was determined to be beneficial to a patient whose analysis revealed any of the following changes: decrease of immunoglobulin IgA, IgG, IgM or IgD free light chain in patient's blood sample; decrease of M-protein as determined by immunofixation in patient's blood sample; decrease of M-protein as determined by electrophoresis in patient's blood sample; decrease of LDH, soluble syndecan-1 or Beta-2 microglobulin in patient's blood sample; decrease as determined by flow cytometry in patient's lymphocyte cell count; decrease of Bence-Jones protein as detected by immunofixation or electrophoresis in patient's urine sample; decrease of percentage of plasma cells or lymphocyte cells, PCLI, Ki-67 or BlyS/APRIL receptors in patient's bone marrow sample. Patients with beneficial outcome of the first cycle of treatment with TACI-Fc5 were subjected to at least two additional cycles of the treatment.

Example 5

Further Treatment of Patients with Initial Beneficial Response to Taci-Fc5 Treatment Patients who showed improvement or at least stabilization of their disease were subjected to at least two more rounds of injections with TACI-Fc5 (FIG. 4). Dose levels initially administered were 2, 4, 7 or 10 mg/kg (FIG. 4). TACI-Fc5 was administered by subcutaneous injection on days 1, 8, 15, 22 and 29 of a 57-day cycle (FIG. 5). Patients were monitored throughout each cycle. General toxicity was assessed using the CTCAE criteria and hematological toxicities using the Cheson (1996) criteria. Dose limiting toxicities include >grade 3 non-hematological or >grade 3 hematological toxicity except those related to lymphopenia. A full PK profile was assessed after the 1st and 5th injections. The biological parameter assessment comprised the M protein, serum and urinary free light chains, soluble syndecan-1, beta 2-microglobulin, polyclonal immunoglobulins, C-reactive protein and lymphocyte subpopulation counts by FACS analysis. Usual safety parameters were assessed, including potential anti-TACI antibodies. Evaluation of response was assessed using modified Bladé criteria at the end of cycles 1 and 3. Patient's condition was classified as improving or at least stabilized if any of the following was detected: decrease of immunoglobulin IgA, IgG, IgM or IgD free light chain in patient's blood sample; decrease of M-protein as determined by immunofixation in patient's blood sample; decrease of M-protein as determined by electrophoresis in patient's blood sample; decrease of LDH, soluble syndecan-1 or Beta-2 microglobulin in patient's blood sample; decrease as determined by flow cytometry in patient's lymphocyte cell count; decrease of Bence-Jones protein as detected by immunofixation or electrophoresis in patient's urine sample; decrease of plasma cells or lymphocyte cells, PCLI, Ki-67 or BlyS/APRIL receptors in patient's bone marrow sample of percentage.

What is claimed is:

1. A method of treating a multiple myeloma, comprising administering to a human patient with multiple myeloma who has become resistant to or who has failed to respond to at least one other method of treatment of the multiple myeloma a composition comprising a fusion molecule selected from the group consisting of:
 (a) a fusion molecule comprising
  (i) TACI extracellular domain wherein said TACI extracellular domain is at least 95% identical to SEQ ID NO:1 and binds BlyS; and
  (ii) a human immunoglobulin-constant domain;
 (b) a fusion molecule comprising amino acids 30-110 of SEQ ID NO: 1 and a human immunoglobulin-constant domain;
 (c) a fusion molecule consisting of amino acids 30-110 of SEQ ID NO: 1 and a human immunoglobulin-constant domain;
 (d) a fusion molecule consisting of SEQ ID NO: 2; and
 (e) a fusion molecule consisting of amino acids 30-110 of SEQ ID NO:1 and the human immunoglobulin-constant domain of SEQ ID NO: 2;
 wherein said composition is administered in an amount from 2.0 mg per 1 kg of patient's body weight to 10 mg per 1 kg of patient's body weight and wherein said composition is administered weekly.

2. A method of treating Waldenström's macroglobulinemia, comprising administering to a human patient with Waldenström's macroglobulinemia who has become resistant to or who has failed to respond to at least one other method of treatment of the Waldenström's macroglobulinemia a composition comprising a fusion molecule selected from the group consisting of:
 (a) a fusion molecule comprising
  (i) TACI extracellular domain wherein said TACI extracellular domain is at least 95% identical to SEQ ID NO:1 and binds BlyS; and
  (ii) a human immunoglobulin-constant domain;
 (b) a fusion molecule comprising amino acids 30-110 of SEQ ID NO: 1 and a human immunoglobulin-constant domain;
 (c) a fusion molecule consisting of amino acids 30-110 of SEQ ID NO: 1 and a human immunoglobulin-constant domain;
 (d) a fusion molecule consisting of SEQ ID NO: 2; and
 (e) a fusion molecule consisting of amino acids 30-110 of SEQ ID NO:1 and the human immunoglobulin-constant domain of SEQ ID NO: 2;
 wherein said composition is administered in an amount from 2.0 mg per 1 kg of patient's body weight to 10 mg per 1 kg of patient's body weight and wherein said composition is administered weekly.

3. The method of claim 1 or 2, wherein said composition is administered in said amount at least 5 times.

4. The method of claim 1 or 2, wherein said composition is administered in said amount during multiple cycles, wherein each cycle comprises administering said composition in said amount 5 times.

5. The method of claim 1 or 2, said method further comprises administering to said patient a medicament.

6. The method of claim 5, wherein the medicament is selected form the group consisting of bisphosphonate, erythropoietin, granulocyte growth factors, granulocyte colony stimulating factor, drugs for the management of pain, melphalan, vincristine, doxorubicin, thalidomide, nucleoside analogs and protesome inhibitors, including but not limited to bortezomib.

7. The method of claim 1 or 2, wherein said composition is administered subcutaneously, orally or intravenously.

8. The method of claim 1 or 2, wherein said human immunoglobulin-constant domain is a human immunoglobulin-constant domain of IgG.

9. The method of claim 8, wherein said human immunoglobulin-constant domain comprises Fc5.

10. A method of treating a multiple myeloma, comprising administering to a human patient with multiple myeloma who has become resistant to or who has failed to respond to at least one other method of treatment of the multiple myeloma a composition comprising a fusion molecule selected from the group consisting of:
 (a) a fusion molecule comprising amino acids 30-110 of SEQ ID NO: 1 and a human immunoglobulin-constant domain;
 (b) a fusion molecule consisting of amino acids 30-110 of SEQ ID NO: 1 and a human immunoglobulin-constant domain; and
 (c) a fusion molecule consisting of SEQ ID NO: 2;
 wherein said composition is administered in an amount from 2.0 mg per 1 kg of patient's body weight to 10 mg per 1 kg of patient's body weight and wherein said composition is administered weekly.

11. A method of treating Waldenström's macroglobulinemia, comprising administering to a human patient with Waldenström's macroglobulinemia who has become resistant to or who has failed to respond to at least one other method of treatment of the Waldenström's macroglobulinemia a composition comprising a fusion molecule selected from the group consisting of:
 (a) a fusion molecule comprising amino acids 30-110 of SEQ ID NO: 1 and a human immunoglobulin-constant domain;

(b) a fusion molecule consisting of amino acids 30-110 of SEQ ID NO: 1 and a human immunoglobulin-constant domain; and (c) a fusion molecule consisting of SEQ ID NO: 2;

wherein said composition is administered in an amount from 2.0 mg per 1 kg of patient's body weight to 10 mg per 1 kg of patient's body weight and wherein said composition is administered weekly.

12. The method of claim 10 or claim 11, said method further comprising administering to said patient a medicament.

13. The method of claim 12, wherein the medicament is selected form the group consisting of bisphosphonate, erythropoietin, granulocyte growth factors, granulocyte colony stimulating factor, drugs for the management of pain, melphalan, vincristine, doxorubicin, thalidomide, nucleoside analogs and protesome inhibitors, including but not limited to bortezomib.

14. The method of claim 10 or claim 11, wherein said composition is administered subcutaneously, orally or intravenously.

15. The method of claim 10 or claim 11, wherein said human immunoglobulin-constant domain is a human immunoglobulin-constant domain of IgG.

16. The method of claim 15, wherein said human immunoglobulin-constant domain comprises Fc5.

* * * * *

SEQUENCE LISTING

```
<160> NUMBER OF SEQ ID NOS: 2

<210> SEQ ID NO 1
<211> LENGTH: 154
<212> TYPE: PRT
<213> ORGANISM: Homo sapiens

<400> SEQUENCE: 1

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
```

```
            50                  55                  60
Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Gly His Arg Gly Ser
    130                 135                 140

Glu Ala Ser Pro Ala Leu Pro Gly Leu Lys
145                 150

<210> SEQ ID NO 2
<211> LENGTH: 348
<212> TYPE: PRT
<213> ORGANISM: Homo sapiens

<400> SEQUENCE: 2

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
             20                  25                  30

Phe Arg Arg Ala Met Arg Ser Cys Pro Glu Glu Gln Tyr Trp Asp Pro
         35                  40                  45

Leu Leu Gly Thr Cys Met Ser Cys Lys Thr Ile Cys Asn His Gln Ser
 50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
                 85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270
```

-continued

```
Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```